(12) United States Patent
Venturelli et al.

(10) Patent No.: US 7,722,659 B2
(45) Date of Patent: May 25, 2010

(54) ENDOLUMINAL PROSTHESIS

(75) Inventors: Andrea Venturelli, Brescia (IT);
Roberto Ghidini, Brescia (IT)

(73) Assignee: Invatec S.r.l., Roncadelle, Brescia (IT)

( * ) Notice: Subject to any disclaimer, the term of this patent is extended or adjusted under 35 U.S.C. 154(b) by 585 days.

(21) Appl. No.: 11/568,468

(22) PCT Filed: May 5, 2004

(86) PCT No.: PCT/IT2004/000249

§ 371 (c)(1),
(2), (4) Date: Jan. 23, 2007

(87) PCT Pub. No.: WO2005/104991

PCT Pub. Date: Nov. 10, 2005

(65) Prior Publication Data

US 2009/0182414 A9     Jul. 16, 2009

(51) Int. Cl.
*A61F 2/06*     (2006.01)

(52) U.S. Cl. .................................... 623/1.15

(58) Field of Classification Search ........ 623/1.11–1.34
See application file for complete search history.

(56) References Cited

U.S. PATENT DOCUMENTS

| | | | |
|---|---|---|---|
| 4,665,771 A | 5/1987 | Mitchell | |
| 4,665,905 A | 5/1987 | Brown | |
| 4,925,445 A | 5/1990 | Sakamoto et al. | |
| 6,464,720 B2 * | 10/2002 | Boatman et al. | 623/1.15 |
| 6,926,734 B1 * | 8/2005 | Klein | 623/1.34 |
| 7,247,166 B2 * | 7/2007 | Pienknagura | 623/1.15 |
| 7,273,494 B2 * | 9/2007 | Rolando et al. | 623/1.15 |
| 7,331,986 B2 * | 2/2008 | Brown et al. | 623/1.15 |
| 7,381,217 B2 * | 6/2008 | Tischler | 623/1.16 |
| 2001/0027339 A1 * | 10/2001 | Boatman et al. | 623/1.15 |
| 2002/0007212 A1 | 1/2002 | Brown et al. | |
| 2002/0095208 A1 * | 7/2002 | Gregorich et al. | 623/1.15 |
| 2004/0073291 A1 | 4/2004 | Brown et al. | |
| 2004/0176833 A1 * | 9/2004 | Pavcnik et al. | 623/1.13 |
| 2006/0020322 A1 * | 1/2006 | Leynov et al. | 623/1.15 |
| 2007/0123974 A1 * | 5/2007 | Park et al. | 623/1.16 |
| 2008/0255655 A1 * | 10/2008 | Kusleika et al. | 623/1.11 |
| 2009/0069882 A1 * | 3/2009 | Venturelli et al. | 623/1.16 |

FOREIGN PATENT DOCUMENTS

| | | |
|---|---|---|
| EP | 0928606 | 7/1999 |
| EP | 1356789 | 10/2003 |
| WO | 00/35378 | 6/2000 |
| WO | 20041026176 | 4/2004 |

* cited by examiner

*Primary Examiner*—Suzette J Gherbi
(74) *Attorney, Agent, or Firm*—Shoemaker and Mattare

(57) ABSTRACT

An endoluminal prosthesis, comprising a tubular body, said tubular body developing along a longitudinal axis, said tubular body comprising a plurality of serpentines, which develop along a substantially circumferential direction, each of said serpentines comprising arm portions of a preset width transversal to their main longitudinal extension, and bend portions joining two subsequent arms, at least one bridge, having a main longitudinal extension, connecting two adjacent serpentines, wherein the bends facing an adjacent serpentine are circumferentially staggered relative to the opposite bends of the adjoining serpentine, both when the prosthesis is collapsed and when the prosthesis is expanded or partially expanded, wherein the at least one bridge connecting adjacent serpentines extends substantially straight, and wherein the at least one bridge has a width transversal to its main longitudinal direction of a greater value than the arm width.

103 Claims, 27 Drawing Sheets

ENDOLUMINAL PROSTHESIS

FIELD OF THE INVENTION

The object of the present invention is an endoluminal prosthesis to be used in passages or ducts of a human body, such as to restore the passage in blood vessels narrowed or occluded by diseases such as a stenosis, in bile ducts or other similar organs of living bodies.

The present invention also relates to such type of endoluminal prosthesis which are self-expanding, e.g. made of superelastic or shape memory materials such as Nitinol.

The present invention also relates to an endoluminal prosthesis provided with means for a prompt location thereof, e.g. by radioscopy.

BACKGROUND OF THE INVENTION

Endoluminal prosthesis, i.e. stents, particularly of the self-expanding type, are known for example by U.S. Pat. No. 4,665,771, U.S. Pat. No. 4,665,905, U.S. Pat. No. 4,925,445 or EP-A-0928606.

These endoluminal prosthesis, though being acceptable in many respects, particularly for their great flexibility and resilience, which enable them to be easily positioned in narrow and tortuous passages in their collapsed state, in some cases they are not sufficiently suitable, when expanded, to support the vessel walls, in order to maintain a proper free lumen for blood to pass therethrough.

Furthermore, in some cases the complex geometry of such known stents may be harmful, since it can hang up to or pinch the vessel wall, thus favouring the re-forming of obstructions, such as plaques and stenosis.

OBJECT AND SUMMARY OF THE INVENTION

The problem at the heart of the present invention is to provide an endoluminal prosthesis, having such structural and functional characteristics to overcome the drawbacks mentioned with reference to the prior art.

This problem is resolved by means of an endoluminal prosthesis of the type described in claim 1 or 68.

Further embodiments are described in the secondary claims.

BRIEF DESCRIPTION OF THE DRAWINGS

Further characteristics and the advantages of the prosthesis according to the invention will become apparent from the description given below of the preferred embodiments thereof, being merely illustrative and non-limiting, with reference to the annexed figures, where.

DESCRIPTION OF PREFERRED EMBODIMENTS

With reference to the above mentioned figures, with 500 has been indicated an endoluminal prosthesis as a whole, such as a prosthesis of the self-expanding type for ducts or vessels of living bodies, such as blood vessels and bile ducts or gastro-intestinal ducts or similar.

In accordance with a general embodiment of the present invention, the endoluminal prosthesis comprises a tubular body 502 suitable to turn from a collapsed condition to an expanded or partially expanded condition.

Figure 4A:
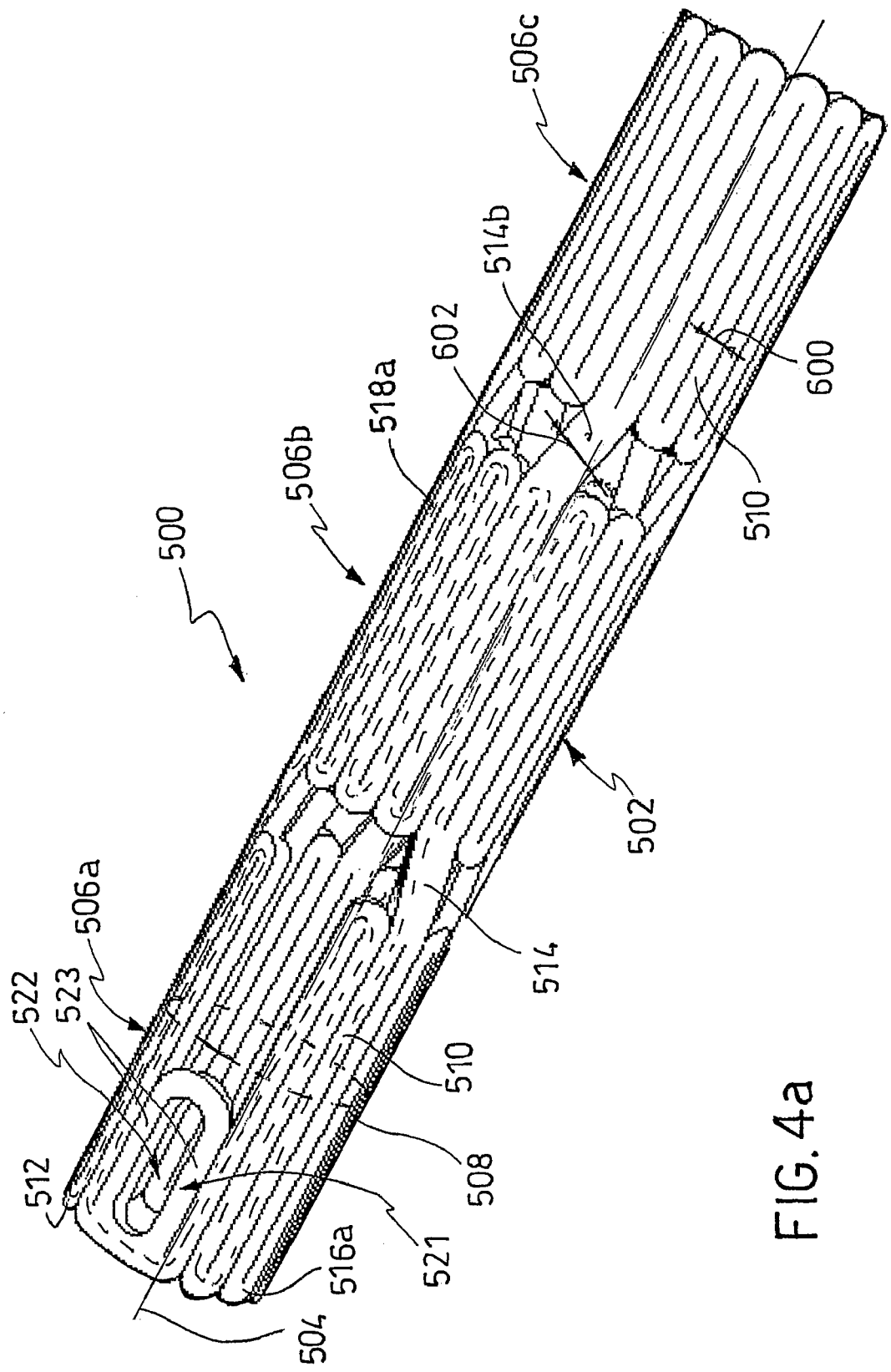
FIG. 4a is a perspective view of a portion of the prosthesis from FIG. 1 in the collapsed state.
Figure 4B:
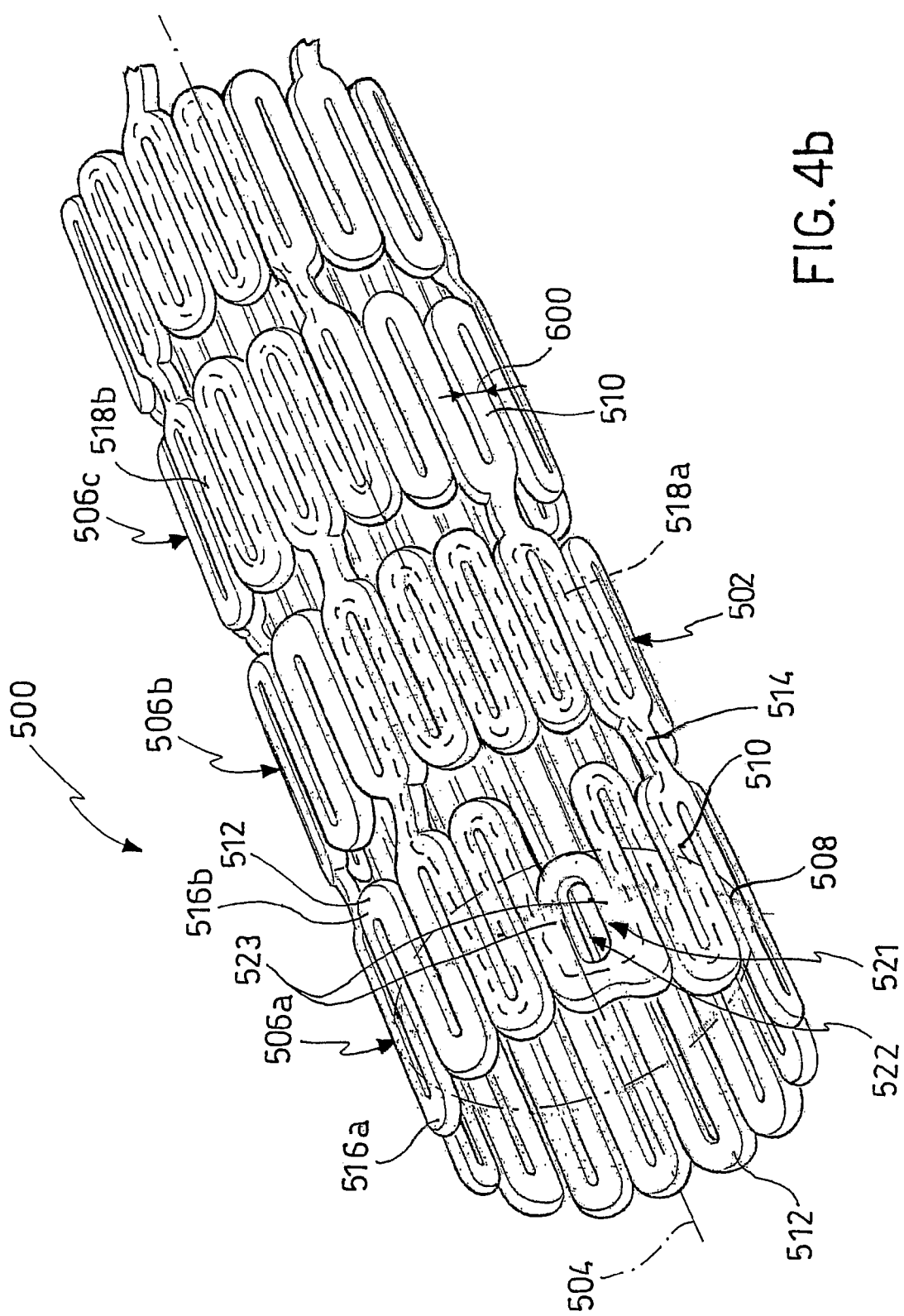
FIG. 4b is a perspective view of the collapsed prosthesis in accordance with a further embodiment.
Figure 21:
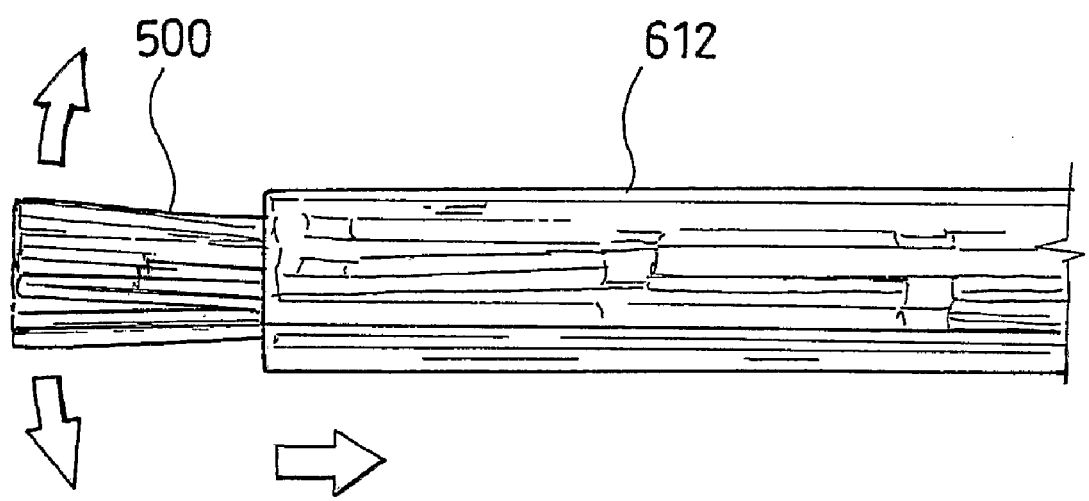
FIGS. 21 to 26 are views of six expansion steps of the prosthesis from FIG. 1.
Figure 22:
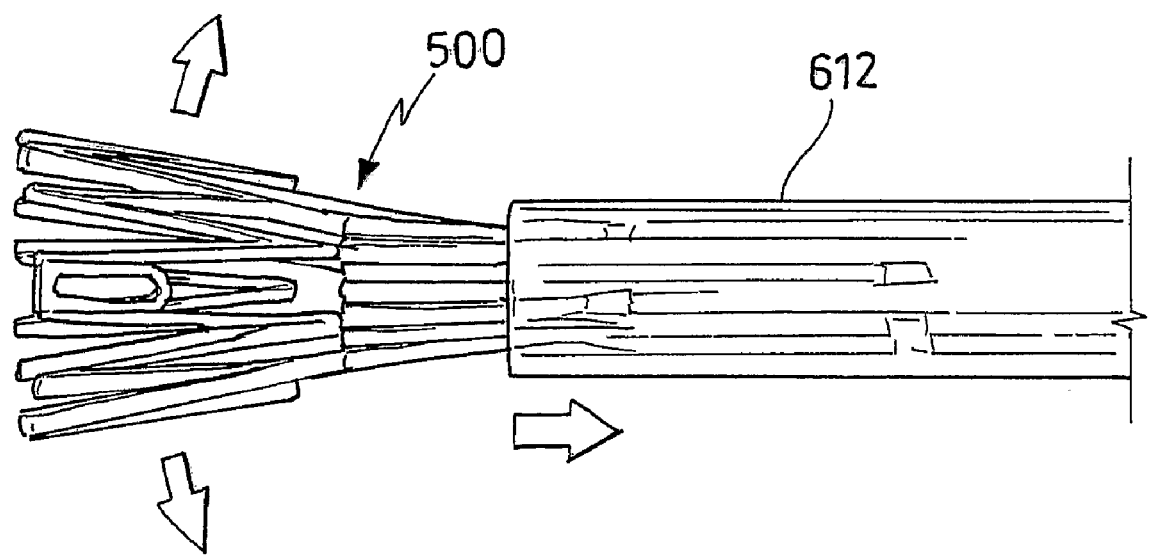
Figure 23:
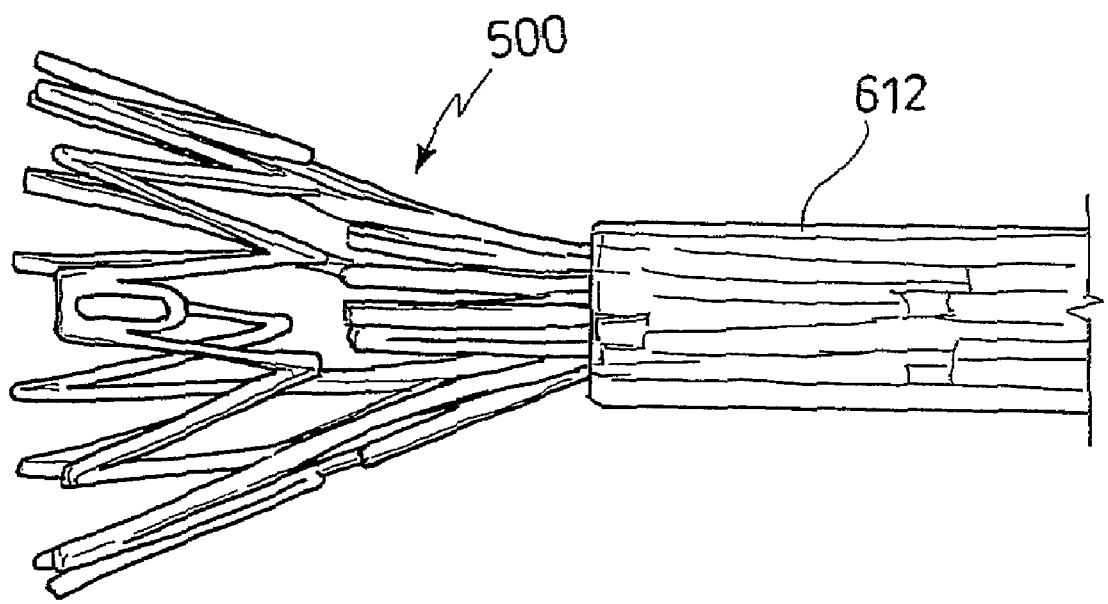
Figure 24:
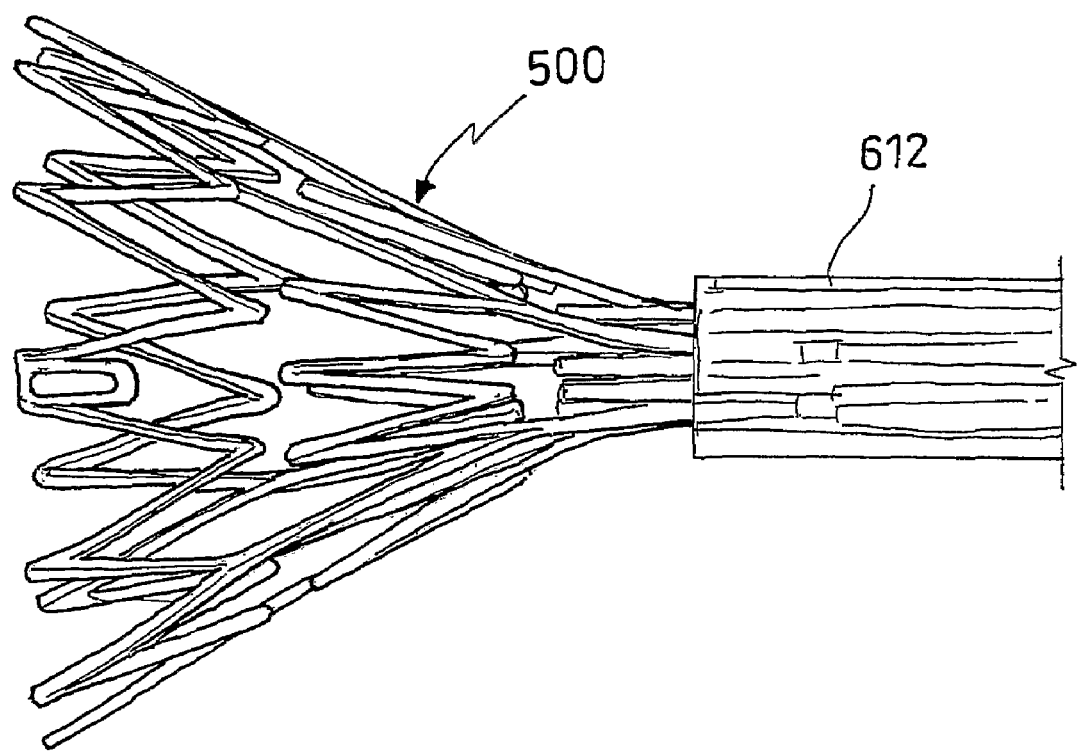
Figure 25:
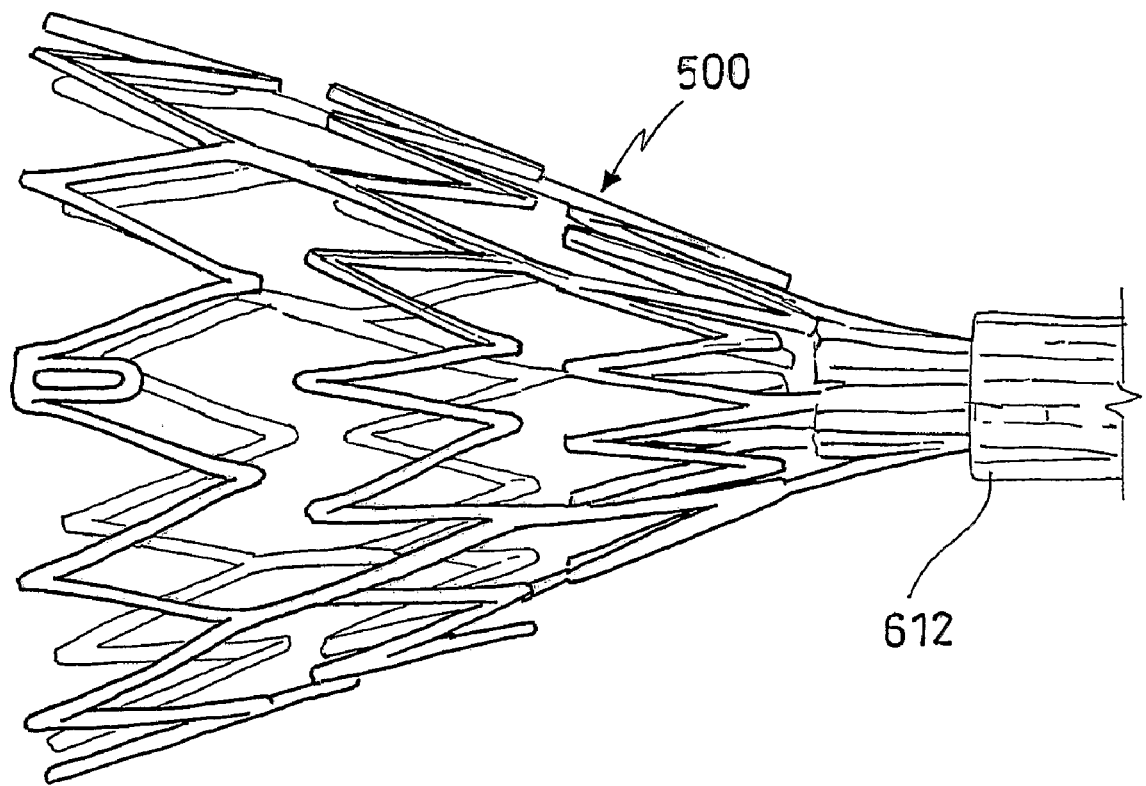

By "collapsed condition" is meant a state of the prosthesis as being contracted such as to have a smaller bulk than in an operating use condition, e.g. a condition where the tubular body 502 has a smaller size or outer diameter than in an operating use condition. For example, the prosthesis is arranged in a collapsed condition when it is either accommodated or arranged on a transport and delivery device suitable to travel along a duct or vessel to the area to be treated. For example, in the case of a self-expanding prosthesis, this is accommodated in a sheath such as to be maintained in the collapsed condition (FIGS. 4 and 21).

Figure 1:
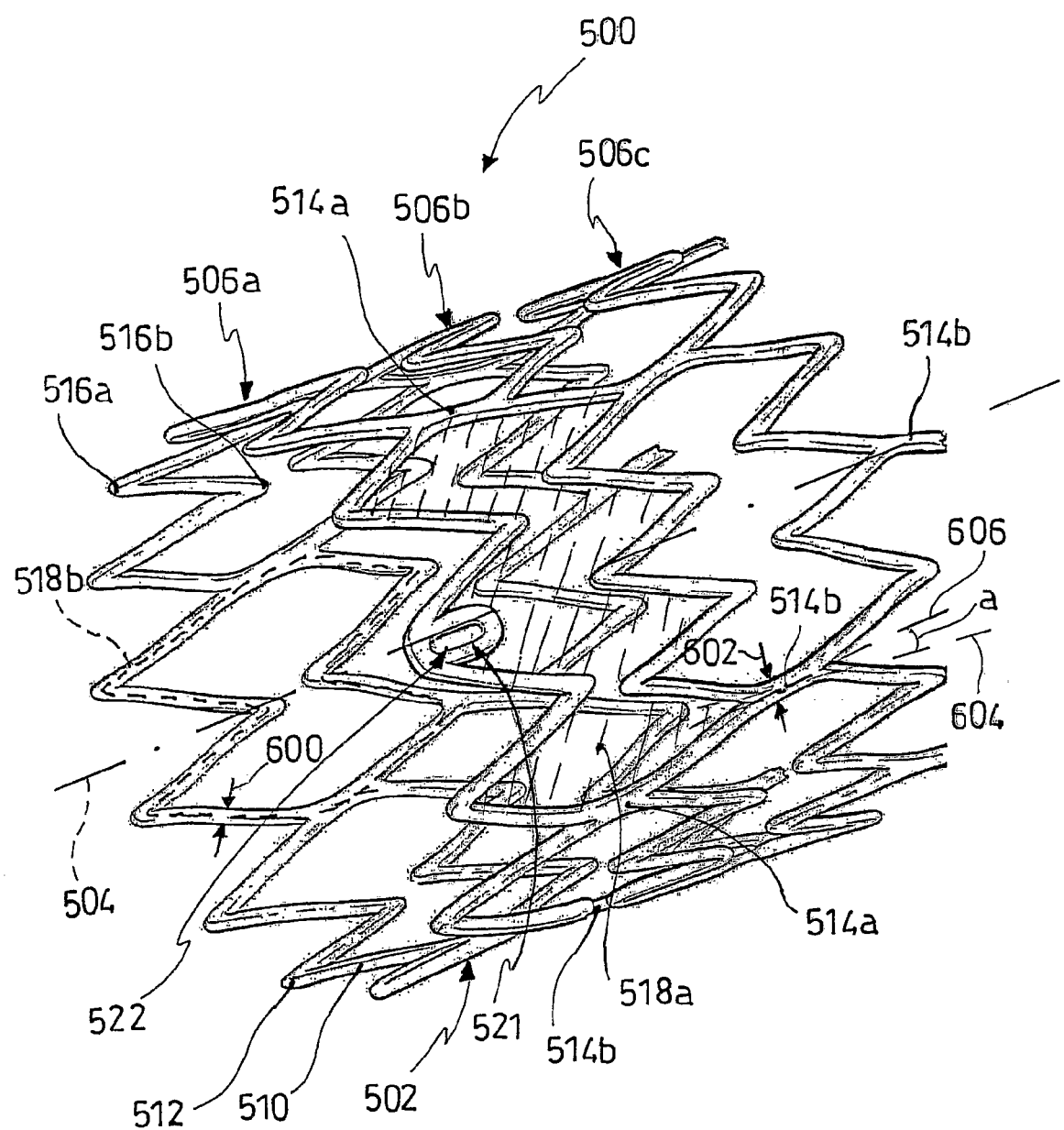
FIG. 1 is a perspective view of an expanded endoluminal prosthesis portion, in accordance with a first embodiment.
Figure 6:
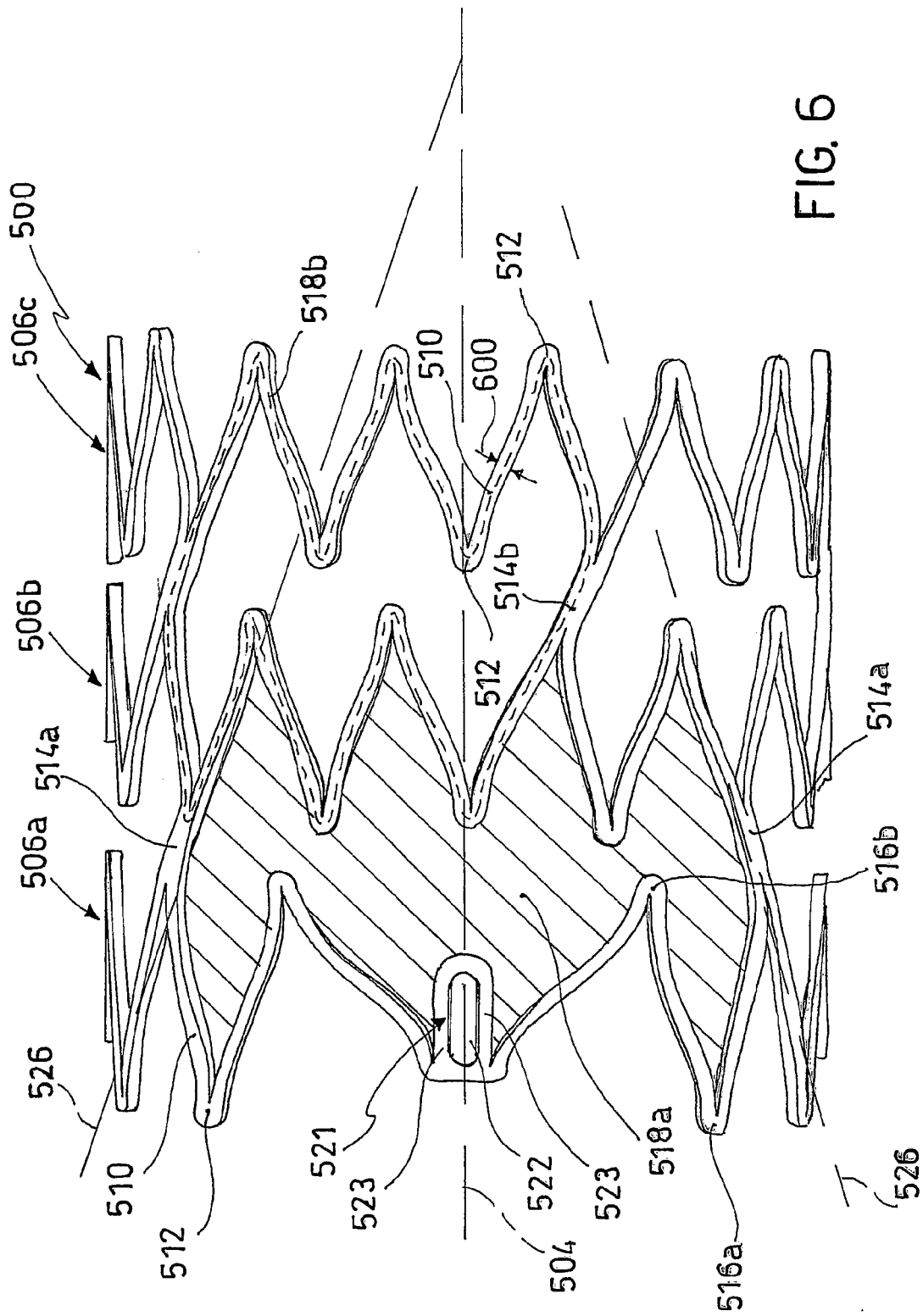
FIG. 6 is a view of a detail of the prosthesis from FIG. 1 when expanded.
Figure 26:
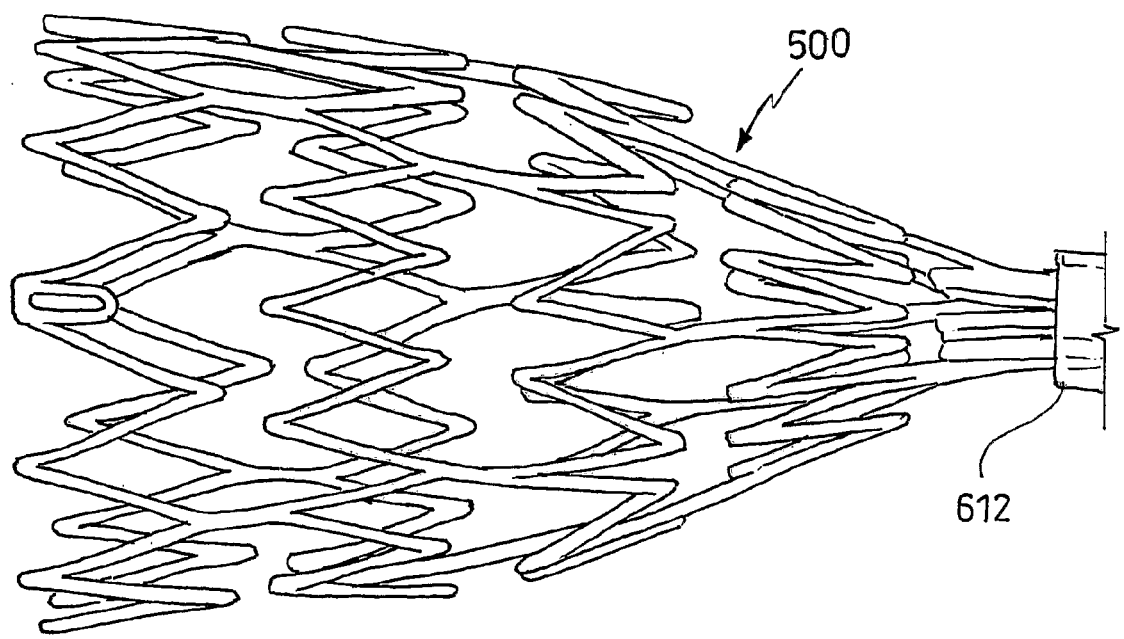

By "expanded or partially expanded condition" is meant a condition where the prosthesis is free from restrictions or an operating use condition with the prosthesis being widened upon pressure contact against the inner surfaces of a duct or vessel walls (FIGS. 1, 6 and 26 where it is illustrated with an expanded and a partially expanded length).

The tubular body 502 develops along a longitudinal axis 504.

By "longitudinal axis" is meant for example either a symmetry axis of a cylindrical body or the stretch axial direction of a tubular body.

The tubular body 502 comprises a plurality of serpentines 506a, 506b, 506c, or closed meander paths, developing along a substantially circumferential direction.

By "serpentine" is meant a zig-zag/to-and-fro developing element around a main direction of stretching.

Each of these serpentines comprising either arm portions or arms 510 of predetermined length 600 transversal to their main longitudinal stretch.

Each of said serpentines 506a, 506b, 506c comprises either bended portions or bends 512, which join two subsequent arms 510 to form said meander path.

Advantageously, at least a bridge 514a, 514b of a main longitudinal stretch connects two adjacent serpentines 506a and 506b or 506b and 506c or 506c and 506b.

With further advantage, the bends 512 facing an adjacent serpentine 506b or 506c are circumferentially staggered 620 relative to the opposite bends 512 of the adjoining serpentine 506b or 506c, both when the prosthesis is collapsed and when the prosthesis is expanded or partially expanded.

Preferably, the at least one bridge 514a and 514b connecting adjacent serpentines 506a and 506b or 506b and 506c or 506c and 506b stretches substantially straight.

Advantageously, the at least one bridge 514a and 514b has a length 602 transversal to its main longitudinal direction which has a greater value than the length 600 of arms 510.

Figure 3:
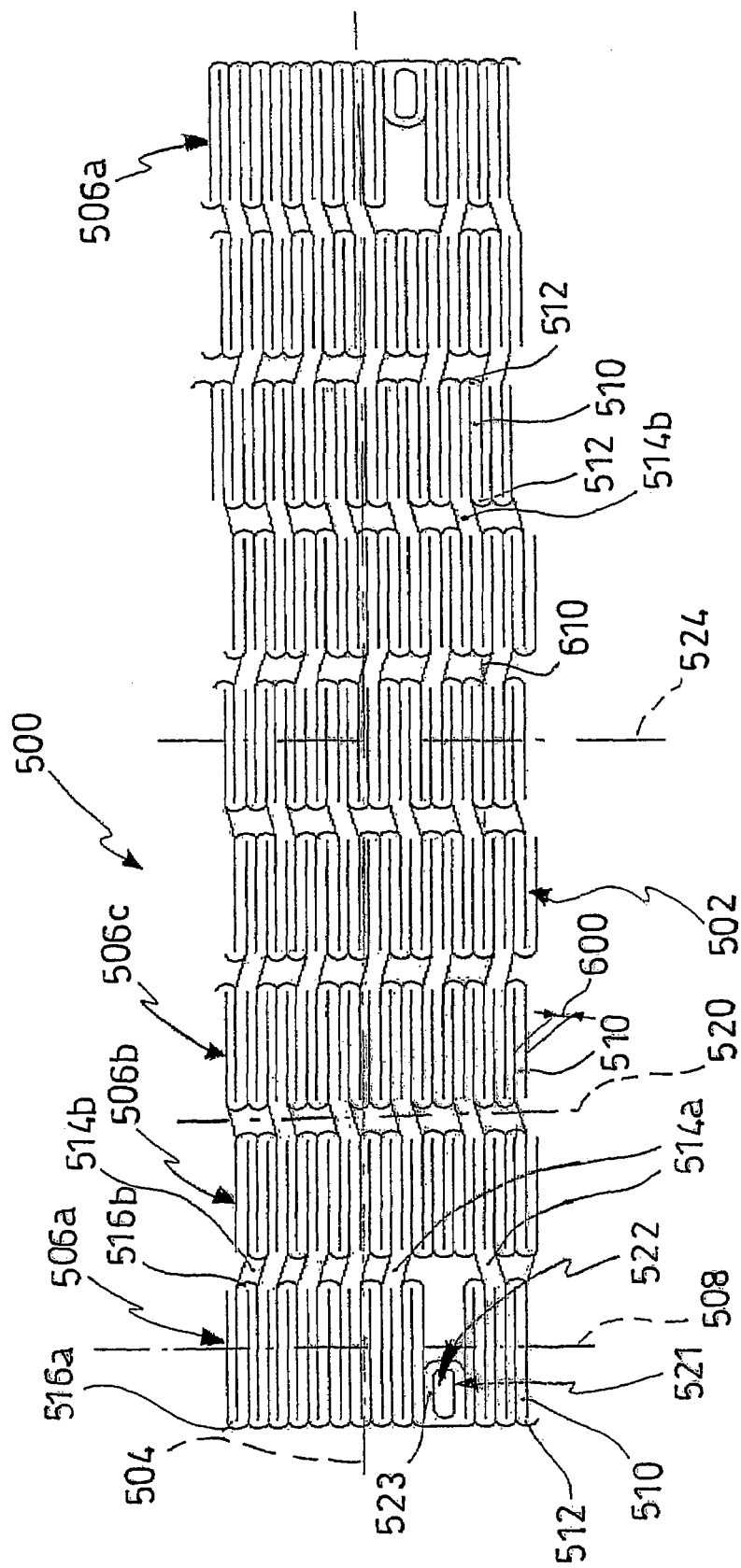
FIG. 3 is a plane development of the prosthesis from FIG. 1 in the collapsed state.

According to a possible embodiment, an endoluminal prosthesis 500 comprises a tubular body 502 developing along a longitudinal axis 504. The tubular body comprises a plurality of serpentines or meander paths 506a, 506b, 506c preferably closed, which develop according to a circumferential direction 508 relative to the direction of the longitudinal axis of the endoluminal prosthesis. The circumferential direction 508 is illustrated in FIG. 4a with reference to the perspective view of the prosthesis in a closed configuration and in FIGS. 3 and 5 with reference to the plane development of the tubular body 502 of the prosthesis in a closed configuration.

A serpentine comprises arms 510 connected by bends 512. According to a possible embodiment, the arms are substantially straight.

Figure 5:
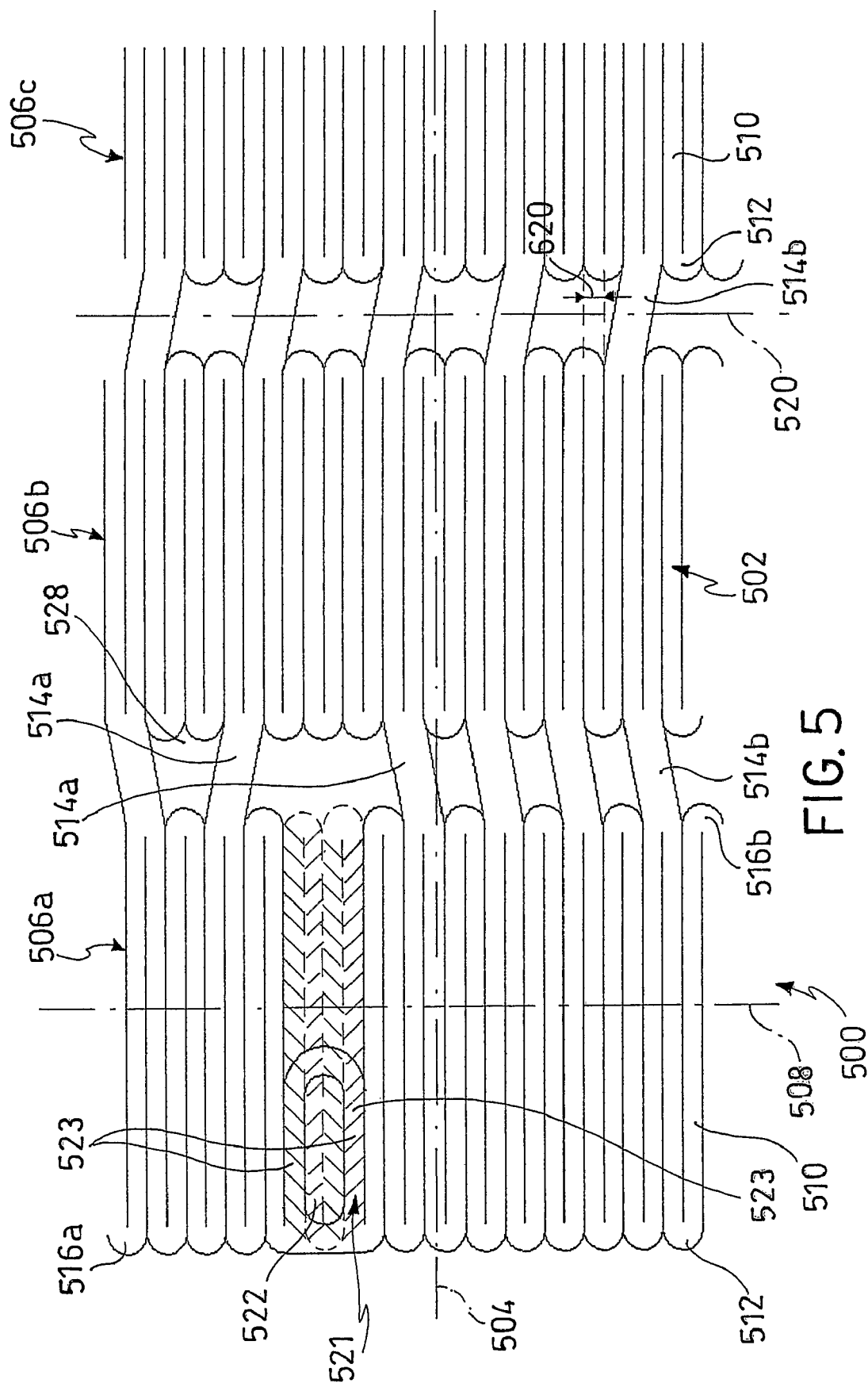
FIG. 5 illustrates a detail of the plane development of the prosthesis from FIG. 1 when collapsed.

In accordance with a possible embodiment, the arms are connected by bends such as to form a sequence of peaks and valleys along the circumferential direction of the corresponding serpentines. With reference to an end portion of a prosthesis such as illustrated in FIG. 1 or 5, for simplicity of exposition those bends being convex towards the outside of the prosthesis will be identified as peaks 516a and those bends being concave towards the outside of the prosthesis, i.e. moving away from a middle axis 524, will be identified as valleys 516b.

Two adjacent serpentines are connected by at least one bridge 514a, 514b thus forming at least two cells between both adjacent serpentines. With "cell" is meant a closed periphery defined by a length of a first serpentine, a first connecting bridge, a length of a second serpentine adjacent to the first one (with the path developing in the opposite way along the circumferential direction) and a second connecting bridge immediately next to the first one.

With references 518a and 518b there have been represented two different cells and the perimeters or areas thereof have been outlined.

According to a possible embodiment, the plurality of serpentines comprise a first serpentine 506a, a second serpentine 506b and a third serpentine, 506c. Preferably, the second serpentine 506b and the third serpentine 506c repeat alternatively along the longitudinal axis. Still more preferably, the second serpentine and the third serpentine are substantially identical. Furthermore, they can be arranged symmetrically relative to a circumferential direction 520 intermediate between both serpentines. With reference to the embodiment illustrated in the figures, the second and third serpentines can be arranged symmetrically relative to a circumferential direction 520 intermediate between both serpentines and staggered to one another along the circumferential direction.

In accordance with one embodiment, said at least one bridge 514 is joined with a bend 512 of a serpentine 506a or 506b or 506c and with a bend 512 of an opposite serpentine 506b or 506c or 506a.

Advantageously, the at least one bridge 514a and 514b has a substantially constant width 602 all along its longitudinal stretch. Preferably, the at least one bridge 514a, 514b has a width 602 substantially equal to twice the width 600 of arms 510. With a further advantage, the at least one bridge 514a and 514b has substantially straight edges. In other words, a bridge 514a, 514b extends without forming any bend, or folds, between a connecting or joint portion thereof to a first serpentine and a second connecting or joint portion thereof to a second serpentine.

In accordance with one embodiment, at least one bridge 514a, 514b is comprised between all the adjacent serpentines 506a, 506b and 506c.

Advantageously, a plurality of bridges 514a, 514b is comprised between adjacent serpentines 506a and 506b or 506b and 506c or 506c and 506b.

In accordance with one embodiment, between at least two adjacent serpentines 506a and 506b or 506b and 506c or 506c and 506b a bridge 514b is provided every four bends 512 as counted along the path of each serpentine.

In accordance with a further embodiment, between at least two adjacent serpentines 506a and 506b or 506b and 506c or 506c and 506b a bridge 514b is provided every six bends 510 as counted along the path of each serpentine.

In accordance with a still further embodiment, between at least two adjacent serpentines 506a and 506b or 506b and 506c or 506c and 506b a bridge 514b is provided every ten bends 510 as counted along the path of each serpentine.

Advantageously, the at least one bridge 514a and 514b develops according to a direction 606 tangential to the tubular body 502 and biased relative to an axis 604 parallel to the longitudinal axis 504 of said body (for example by an angle designated with the reference a or b).

Preferably, all the bridges 514b between at least two adjacent serpentines 506b and 506c are parallel to one another.

In accordance with one embodiment, by going through the prosthesis 500 in a longitudinal way, e.g. from a first proximal end to a second distal end of the prosthesis, one encounter bridges 514b alternating with one another with opposite way direction biases (a and b) relative to an axis 604 parallel to the longitudinal axis of the tubular body.

Advantageously, by going through the prosthesis 500 in a longitudinal way, one encounters the bridges 514b alternating with one another with direction biases a, b of opposite value ("a" having the same value as and opposite way to "b") relative to an axis 604 parallel to the longitudinal axis of the tubular body.

Figure 2:
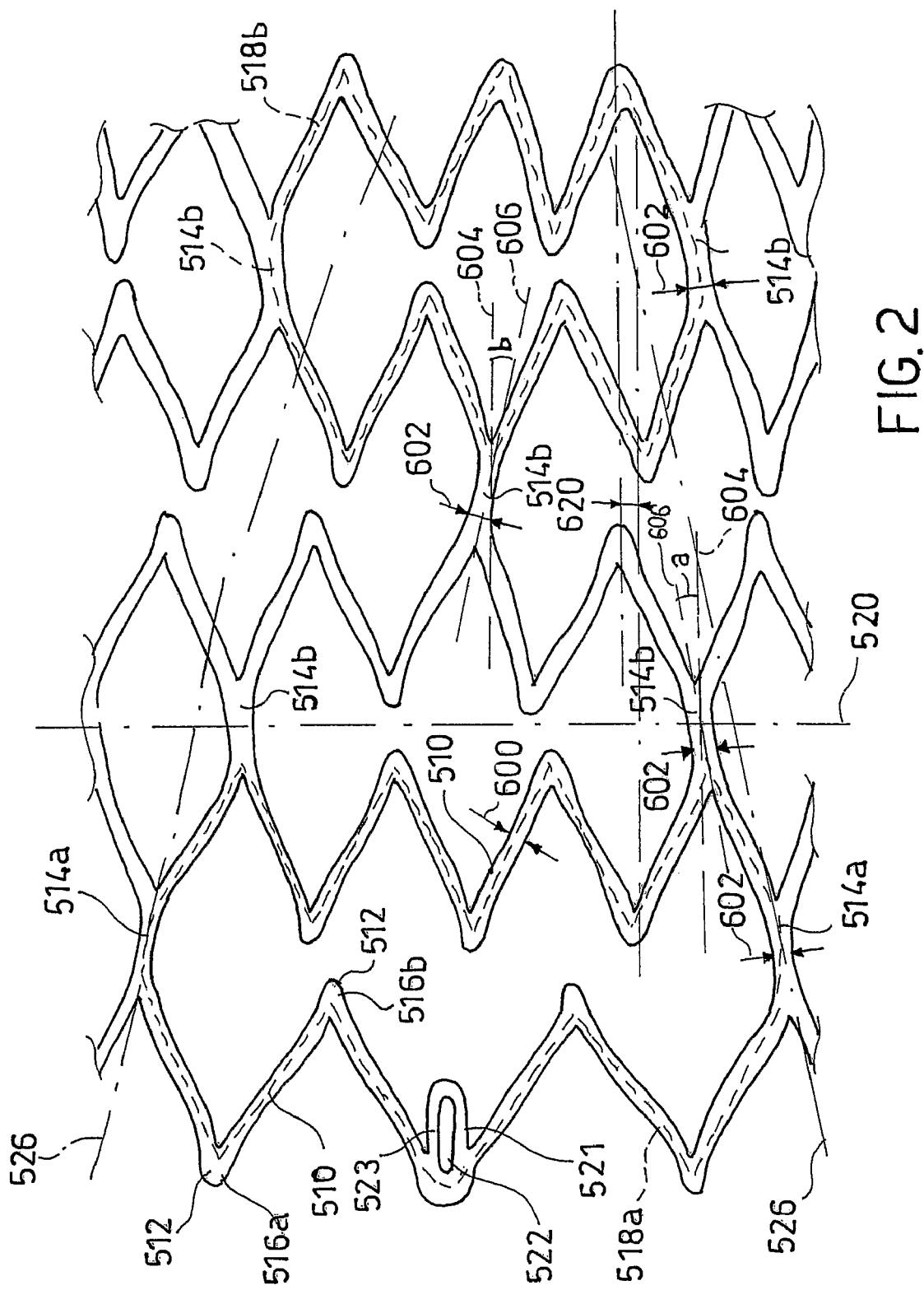
FIG. 2 is a plane development of a portion of the prosthesis from FIG. 1.

In accordance with one embodiment, the prosthesis comprises a cell 518a, 518b comprising opposite lengths of two adjoining serpentines 506a and 506b or 506b and 506c or 506c and 506b comprised between two subsequent bridges 514a, 514b, and said subsequent bridges 514a and 514b forming a closed path (such as indicated by dotted line 518b in FIG. 2).

In accordance with one embodiment, the arms 510 are substantially straight. In other words, an arm extends without forming any bend, or fold, between a connecting or joint portion thereof to a first bend 512 and a second connecting or joint portion thereof to a second bend 512.

Advantageously, the arms 510 comprise substantially straight edges.

In accordance with one embodiment, at least one cell 518b comprises six complete bends 512.

In accordance with a further embodiment, at least one cell 518b comprises ten complete bends 512.

In accordance with a still further embodiment, at least one cell 518b comprises eighteen complete bends 512.

Advantageously, according to one embodiment, at least one prosthesis 500 length, when being in a collapsed state, comprises a plurality of serpentines 506b and 506c equal to one another, having corresponding bends 512, facing the same end as the prosthesis 500, such as the proximal end, either circumferentially aligned with one another, or on the same axis 610 parallel to longitudinal axis 504 of tubular body 502. With further advantage, said at least one length of prosthesis is an intermediate portion of the prosthesis or, preferably, a middle length of the prosthesis 500.

In accordance with one embodiment, said prosthesis 500 is a unique body. For example, said body 502 is obtained by cutting a tubular element, preferably by laser cutting.

Advantageously, said body is made of a superelastic material. In accordance with a different embodiment, said body is made of a strain hardened pseudoelastic material. In other words, a material being in the austenitic state at room temperature (Af<15° C.) when annealed can be used, to which is then applied a sufficient strain hardening, such as greater than 30%, which allows to get 3%-4% elastic recovery after deformation or greater. Preferably, 50% strain hardening is applied.

In accordance with an embodiment, said body 502 is made of a shape memory material.

Advantageously, said body is made of Nitinol, or a Ni and Ti based alloy, such as with Nickel nominal weight percentage of 55.8%.

For example, a material with Austenite-to-Martensite phase transition can be used that, when being in the annealed or stress-relieved state, during a heating of the same the higher temperature of the end of austenite transformation, or Af, is lower than 15° C.

In accordance with one embodiment, the first serpentine 506a comprises at least one frame 521 defining a slot or housing 522. The frame 521 is arranged at a bend between two arms. Particularly, the frame 521 and the slot 522 can be arranged in place of at least two arms and one bend relative to the second or third serpentines.

According to a possible embodiment, the second serpentine and the third serpentine comprise the same number of arms and the same number of bends.

Preferably the frame 521 and the slot 522 are arranged at the bend between two arms in place of four arms and three bends relative to the second or third serpentines. In FIG. 5 the arms and the bends replaced by the slot have been illustrated with a dotted line.

Advantageously the frame 521 occupies the whole length left free by the replaced arms and bends, as measured along the circumferential direction and when the endoluminal prosthesis is in the collapsed condition.

In accordance with a possible embodiment, the slot or housing 522 passes all through the thickness of the tubular body 502.

Advantageously the frame 521 is arranged in the concave part of the bend between both arms directly connected to the frame 521.

According to a possible embodiment, the prosthesis is formed as a unique body from a tubular body 502 by cutting, such as laser cutting of a cylindrical wall thereof.

Advantageously, the frame 521 is formed as a unique body in the tubular body 502 obtained by laser cutting of a cylindrical wall.

In accordance with a possible embodiment, the slot 522 has an elongated shape in the direction of the longitudinal axis of the prosthesis, preferably elliptical or rectangular with short rounded sides. Advantageously, the frame 522 has an elongated shape in the direction of the longitudinal axis of the prosthesis. Preferably the short side of frame 521 corresponding to the bend between both arms directly connected to the frame itself is substantially straight along the circumferential direction, when considered in a plane development of the prosthesis.

Advantageously both arms directly connected to the frame 521 join to the frame itself at end points.

Advantageously the frame 521 comprises two elongated sides 523 having substantially the same width as the arms 510 of the prosthesis, as measured along the circumferential direction 508, and a shorter length than the arms 510 of the prosthesis, as measured along the longitudinal direction 504 thereof.

Advantageously, a radiopaque material is provided within the slot 522, preferably melted within the slot. The radiopaque material may be any material having a greater visibility to X-rays than the material used for the prosthesis.

In the case where the prosthesis is made of a superelastic or shape memory material, such as Nitinol (or an alloy with Ni and Ti as the main part), the radiopaque material can be selected from Tantalum, Gold, Platinum, Tungsten or other materials suitable for the purpose.

According to a possible embodiment, the first serpentine 506a housing the frame 521 is an end serpentine of the prosthesis. Advantageously, both end serpentines of the prosthesis, i.e. the first and last serpentines, comprise at least one frame 521, respectively. In other words, in a possible embodiment of the prosthesis according to the present invention, by going through the prosthesis along the longitudinal axis 504 starting from an end of the prosthesis itself, such as a proximal end, one encounters a first serpentine or end serpentine, a sequence of alternated second and third serpentines and a last serpentine or further end serpentine, or distal end serpentine. In accordance with a possible embodiment, the last serpentine or further end serpentine symmetrically reproduces the first serpentine relative to a middle axis 524 of the prosthesis, possibly staggered along the circumferential direction.

In accordance with an advantageous embodiment, the frame 522 is arranged at an end bend, i.e. a bend belonging to the end serpentine and with its concavity facing the inside of the prosthesis, i.e. the middle axis 524. In other words, the frame 521 is arranged at or in place of a peak 516a, preferably within the concavity thereof.

Considering a cell 518a comprising the frame 521 and defined between a length of the end serpentine 506a and a length of the second serpentine 506b, the frame 521 is advantageously arranged inside the respective cell.

In accordance with a possible embodiment, the frame 521 has an elongated shape in the direction of the longitudinal axis of the prosthesis and develops from the end bend towards a middle axis 524 of the endoluminal prosthesis.

By designating with 518a the cell defined between the first and the second serpentines and comprising the frame 521, this cell comprises two bridges 514a developing along directions 526 tangential to the tubular body. Both bridges 514a may be advantageously arranged along directions 526 substantially parallel to one another and further parallel to the development directions of the remaining bridges 514b between the first and the second serpentines. Still more advantageously, both bridges 514a may be arranged along directions 526 incident to one another, both in a closed configuration and in an expanded configuration of the prosthesis (FIGS. 2, 3).

In accordance with a possible embodiment, the bridges 514a belonging to the cell 518a comprising the frame 521 develop along directions 526 converging from the end of the prosthesis towards a middle axis 524 of the prosthesis itself.

In accordance with an embodiment, the bridges 514a develop according to directions 526 tangential to the tubular body and biased relative to an axis parallel to the longitudinal axis 504 of the endoluminal prosthesis.

Advantageously, the bridges 514a of cell 518a comprising the frame 521 develop along directions 526 tangential to the tubular body and biased relative to the longitudinal axis 504 of the endoluminal prosthesis.

In accordance with a possible embodiment, by designating with 514b the bridges connecting the first and the second serpentines which do not belong to cell 518a comprising the frame 521, these bridges 514b are substantially parallel to at least one of the bridges 514a belonging to the cell 518a comprising the slot 522.

Advantageously, in the cell 518a comprising the frame 521, the number of arms and bends of the first serpentine length is lower than the number of arms and bends of the second serpentine length. For example in the cell 518a comprising the frame 521, the length belonging to the first serpentine may comprise at least two arms and two bends less than the arms and bends of the length belonging to the second serpentine, as symmetrically counted between both serpentines. In the example from FIG. 2, starting from one of the bridges 514a, the length of the first serpentine belonging to the cell 518a containing the slot comprises six arms and five bends while the length of second serpentine belonging to the cell 518 containing the frame 521 comprises eight arms and seven bends.

In FIG. 5 is shown a plane development of a possible embodiment of the endoluminal prosthesis according to the present invention.

According to a possible embodiment, such as illustrated in FIG. 5, with 528 has been designated a further cell of a different shape than the cell 518a containing the frame 521 and the remaining cells 518b of the endoluminal prosthesis. For simplicity of description the further cell 528 will be indicated as the "anomalous" cell.

The anomalous cell 528 is defined between the first and second serpentines and preferably adjacent to the cell 518a containing the slot. Advantageously the anomalous cell 528 shares a bridge 514a with cell 518a containing the slot and preferably shares that bridge which develops along a direction tangential to the tubular body incident to the development directions of the remaining bridges provided between the first and the second serpentines. The "anomalous" cell comprises two arms and two bends more than the remaining cells 518b of the prosthesis. For example, the anomalous cell comprises six arms and five bends on the length relative to the second serpentine while the remaining cells 518b of the prosthesis comprise four arms and three bends, with reference to a length relative to a serpentine.

From what has been discussed above, it should be appreciated that providing an endoluminal prosthesis according to the present invention allows to meet the requirement of visibility to X-rays, or however to radioscopy, of the prosthesis itself while maintaining its structure solid and avoiding that parts may protrude outside the prosthesis.

The original provision of replacing some arms and bends of the serpentine to insert the slot and the radiopaque material enables the prosthesis to deploy evenly all along the longitudinal development thereof, simplifying at the same time the manufacturing steps of the prosthesis itself.

By providing the cell comprising the frame with arms developing along directions tangential to the tubular body which are incident to one another, local distortions due to the difference in arms and bends between the serpentines can be prevented. This aspect is enhanced by the presence of the anomalous cell adjacent to the cell containing the slot.

FIG. 6 illustrates a partial perspective view of the above prosthesis in a deformed configuration with reference to the end comprising the frame 521.

Figure 7:
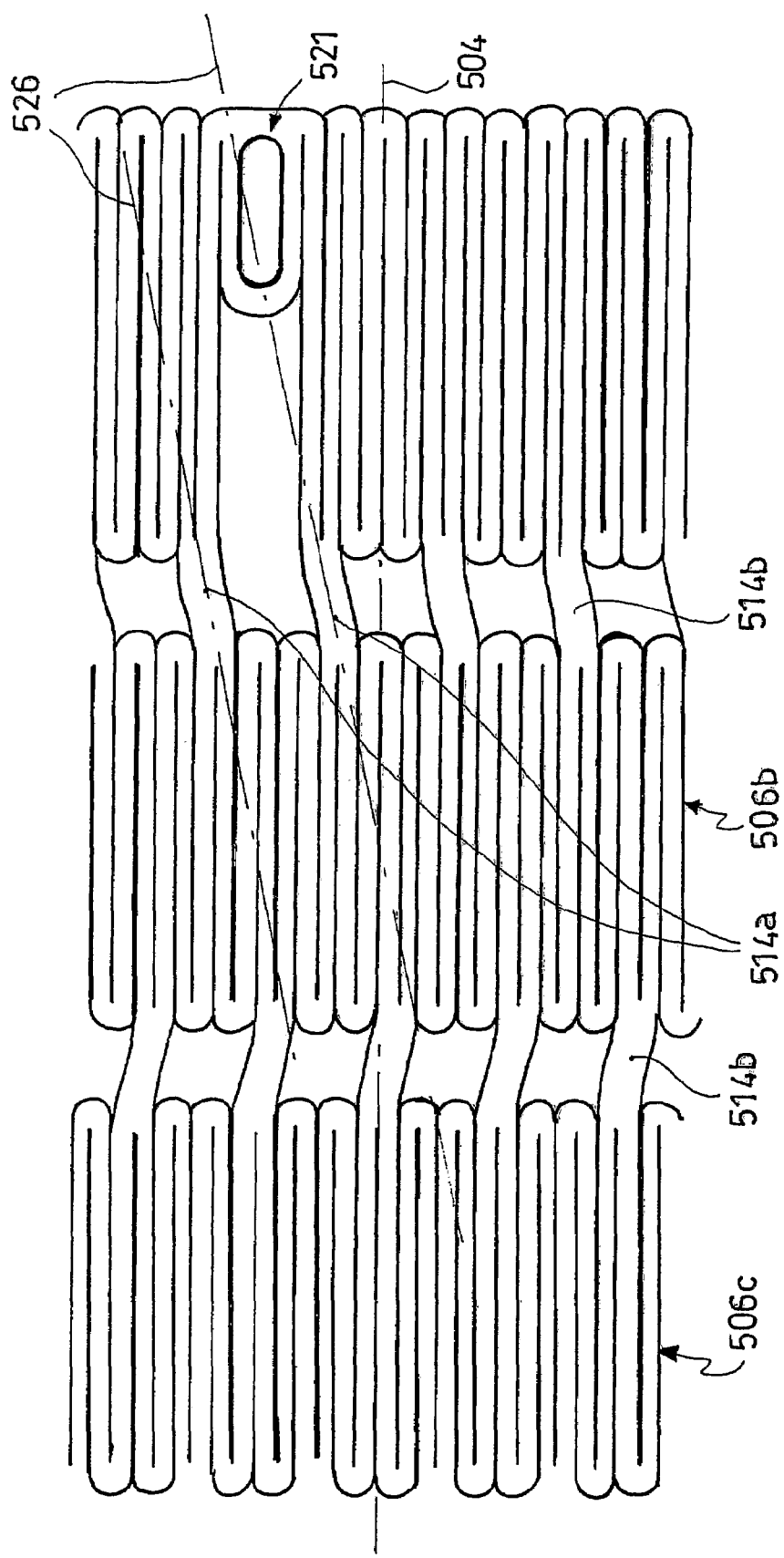
FIG. 7 illustrates a detail of a plane development of a collapsed endoluminal prosthesis according to a further embodiment.
Figure 9:
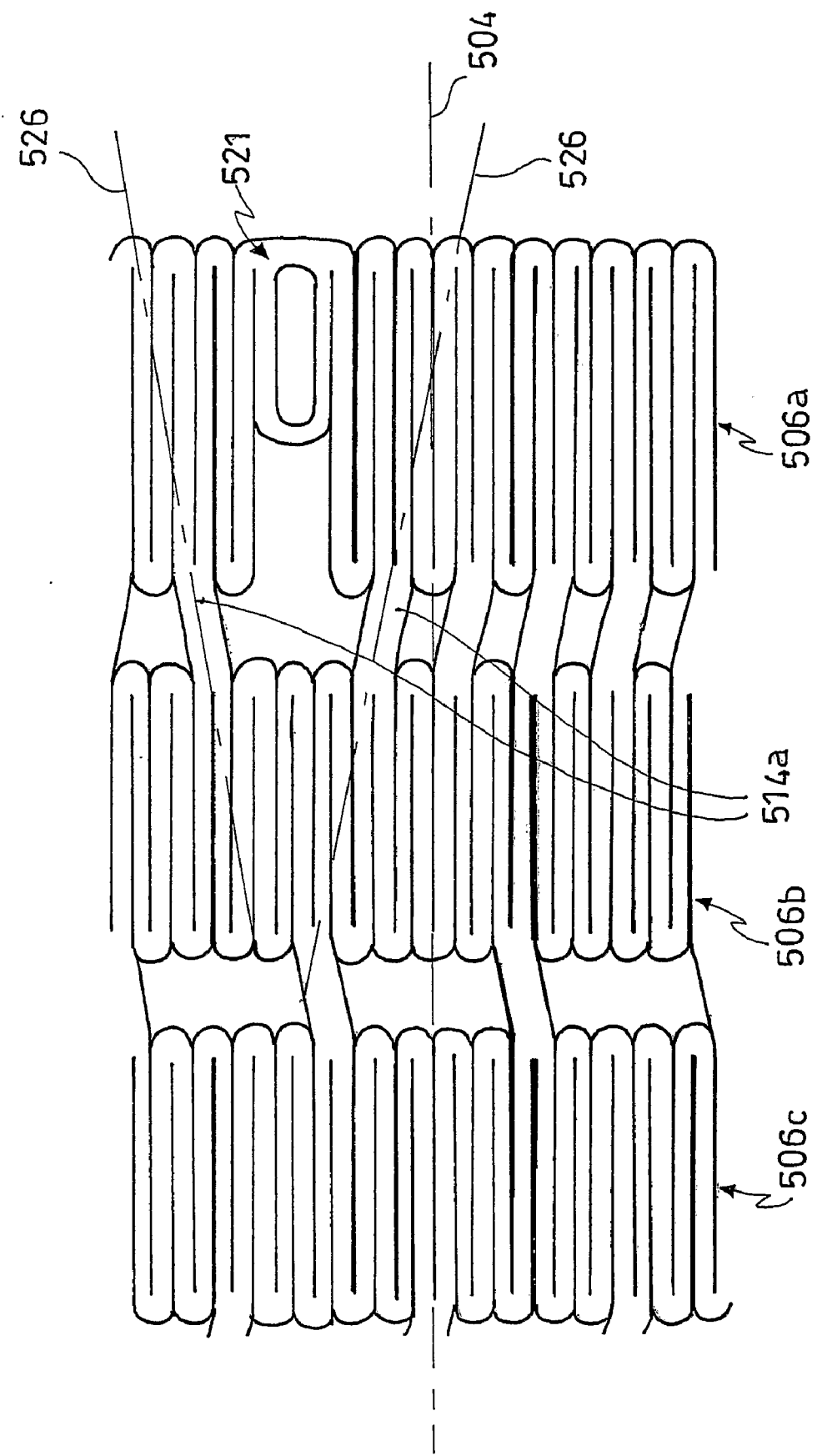
FIG. 9 illustrates a detail of a plane development of a collapsed endoluminal prosthesis according to a still further embodiment.
Figure 11:
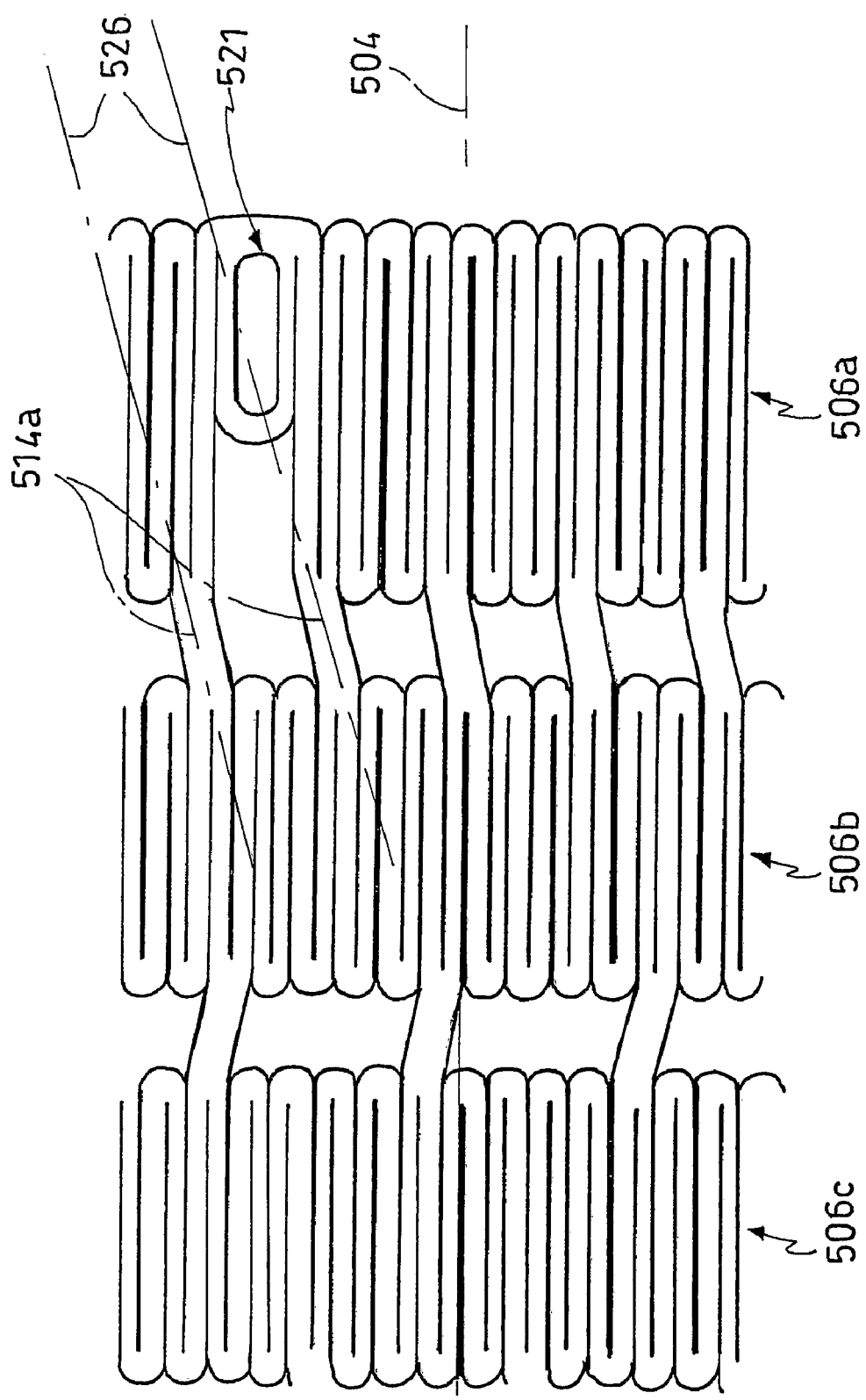
FIG. 11 illustrates a detail of a plane development of a collapsed endoluminal prosthesis according to a further embodiment.

FIGS. 7, 9, 11 illustrate the plane development of respective three possible embodiments of the prosthesis according to the present invention. FIG. 7 represents an embodiment similar to that of FIG. 3 or 5 wherein the bridges 514a corresponding to the cell comprising the frame 521 develop along directions 526 tangential to the tubular body, biased relative to the longitudinal axis 504 and parallel to one another. These directions are further parallel to the tangential directions along which the other bridges 514b develop between the first and second serpentines. FIGS. 9 and 11 represent two types of prosthesis where the cells defined between the second and third serpentines are of a different configuration compared to that of the cells between the second and third serpentines of the embodiments from FIG. 3, 5 or 7. Furthermore, the prosthesis from FIG. 9 has the bridges of cell 518a containing the frame 521 that develop along directions 526 tangential to the tubular body and biased relative to the longitudinal axis and incident to one another. On the other hand, in the prosthesis from FIG. 11 the bridges of the cell 518a containing the frame 521 develop along directions 526 tangential to the tubular body and biased relative to the longitudinal axis and parallel to one another.

Figure 8:
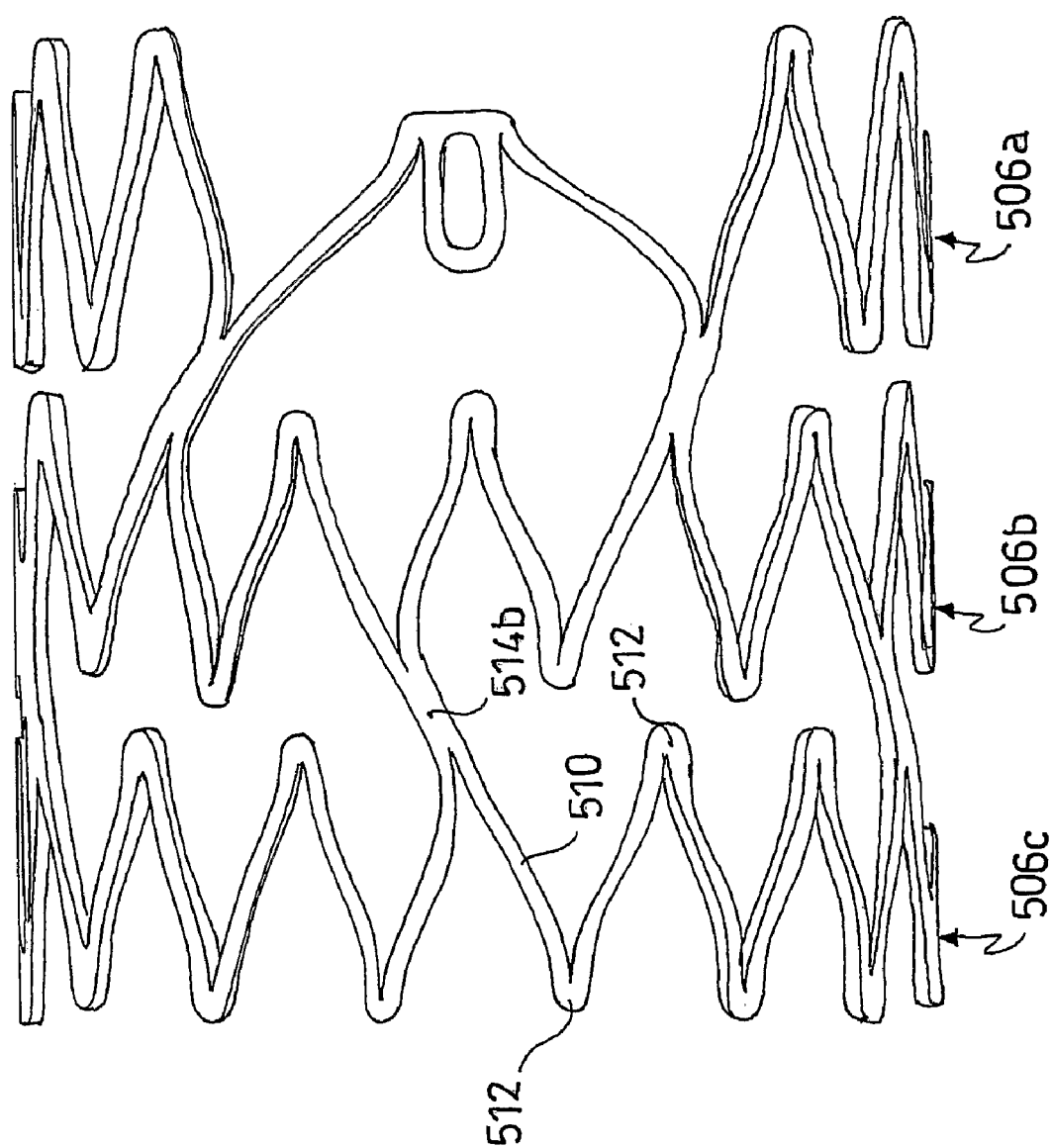
FIG. 8 is a view of a detail of the prosthesis from FIG. 7 when expanded.
Figure 10:
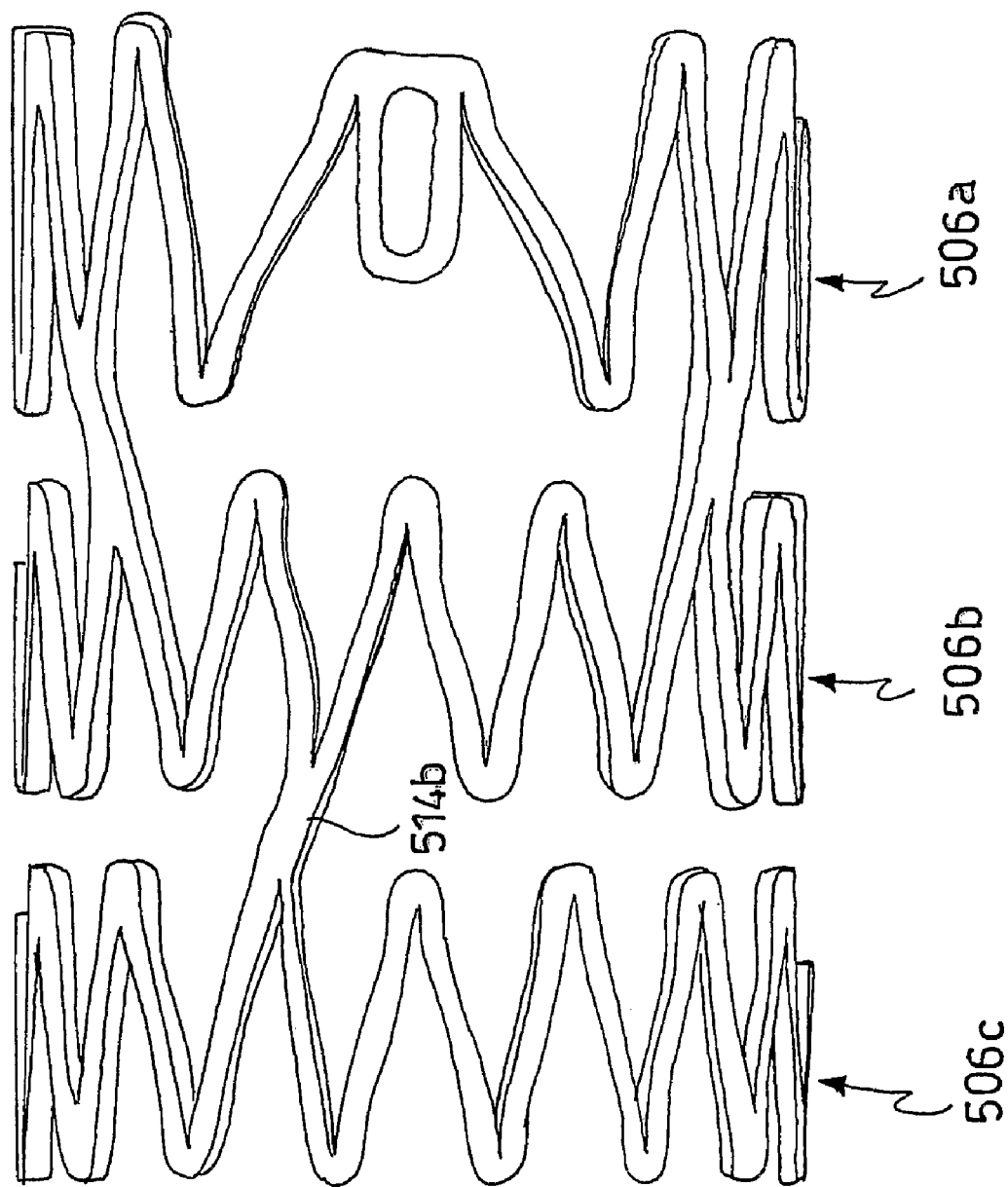
FIG. 10 is a view of a detail of the prosthesis from FIG. 9 when expanded.
Figure 12:
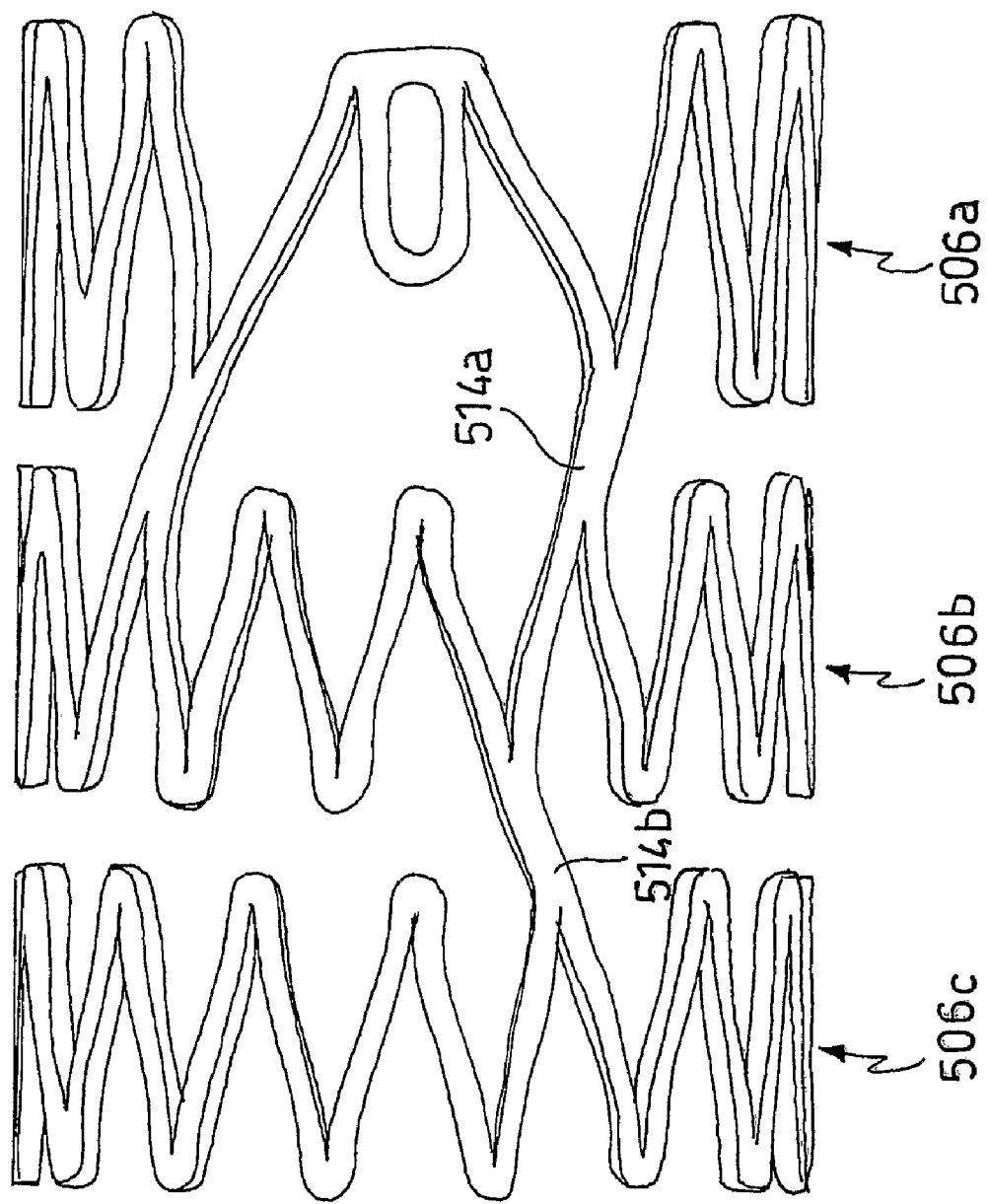
FIG. 12 is a view of a detail of the prosthesis from FIG. 11, when expanded.

FIGS. 8, 10, 12 illustrate the prosthesis from FIGS. 7, 9, 11 respectively, in an expanded or widened configuration.

Figure 13:
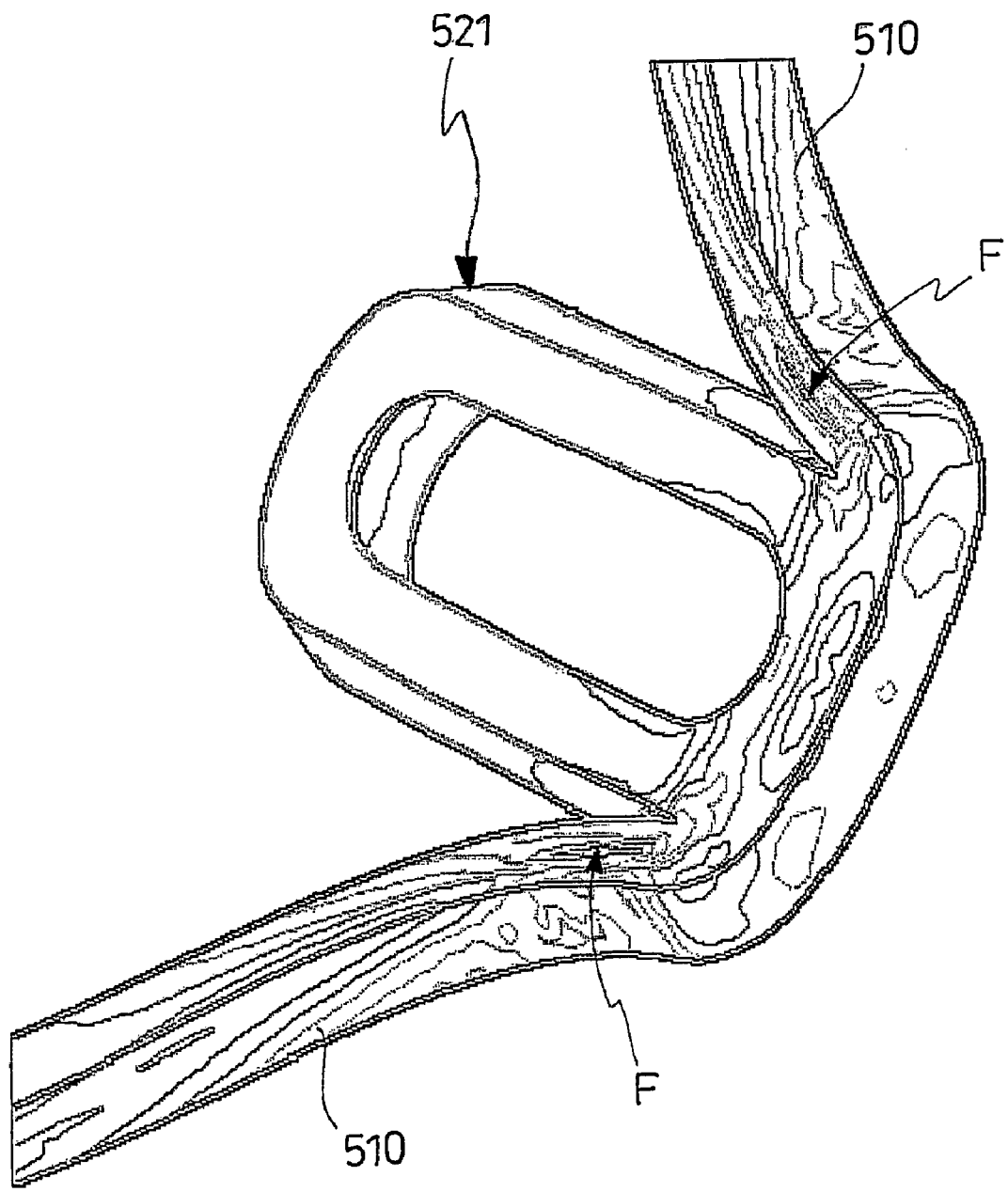
FIGS. 13 and 14 are perspective views of a detail of the prosthesis from FIG. 1 when expanded, wherein the stress condition and the corresponding strain condition are highlighted.
Figure 14:
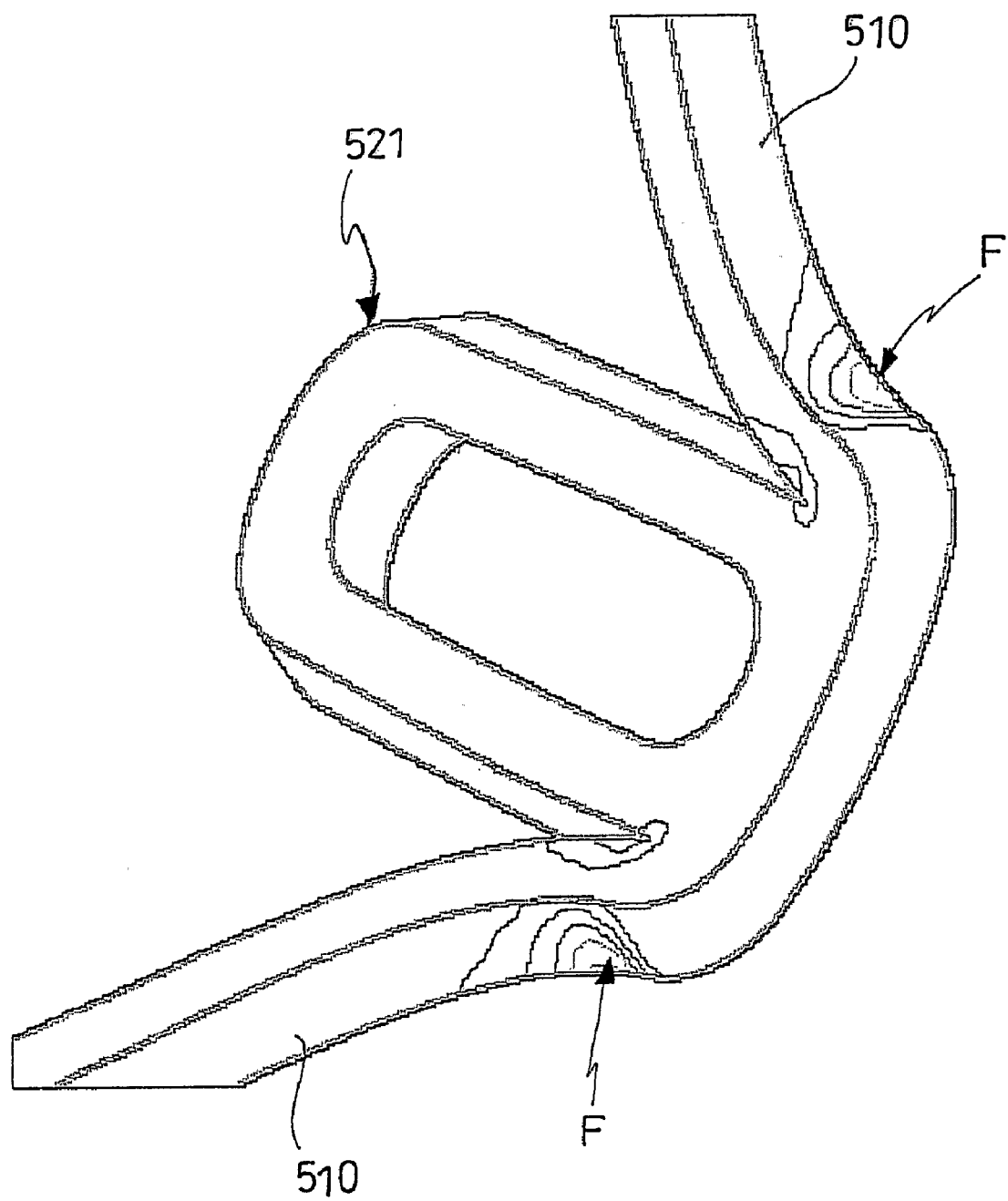
Figure 15:
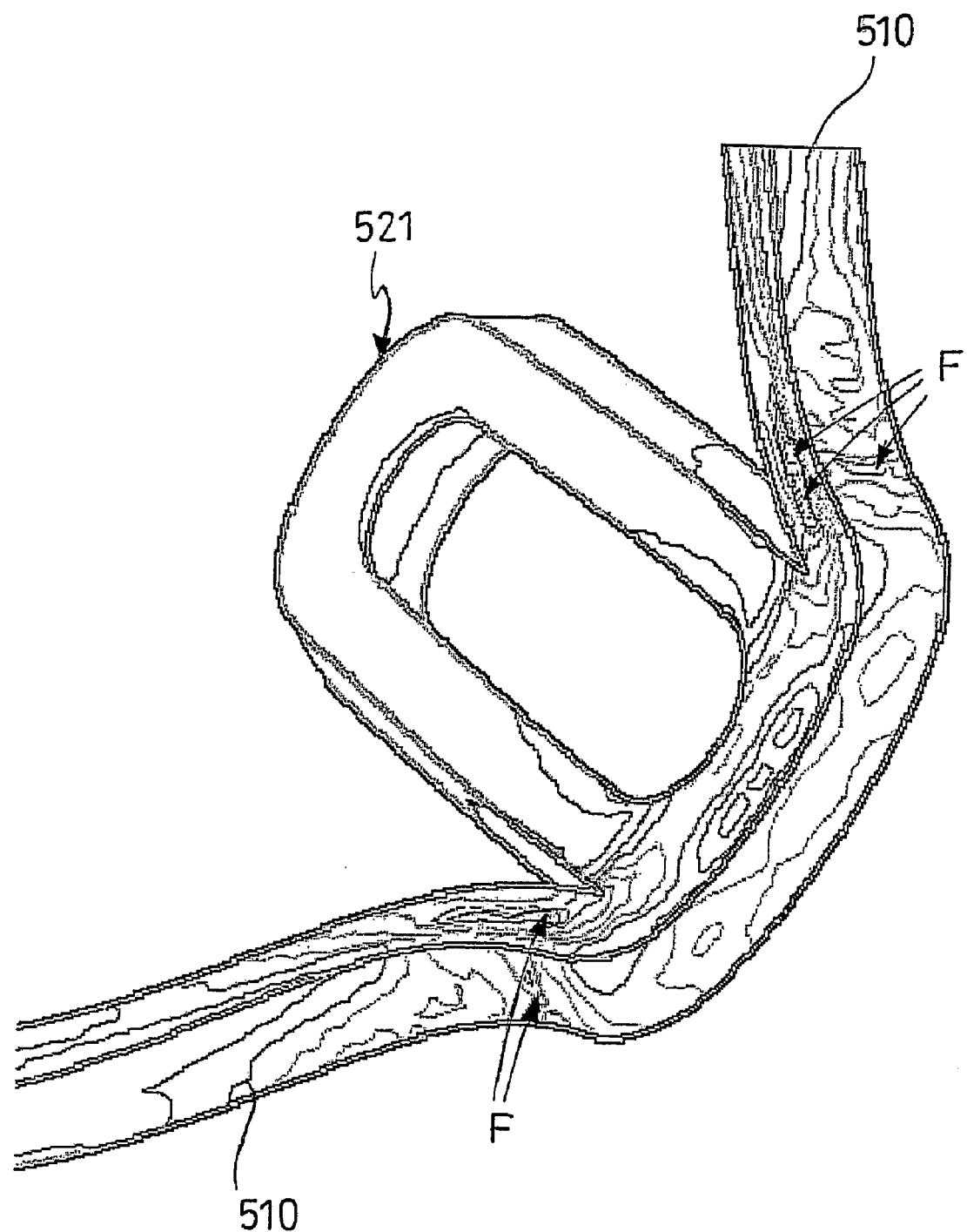
FIGS. 15 and 16 are perspective views of a detail of the prosthesis from FIG. 7 when expanded, wherein the stress condition and the corresponding strain condition are highlighted.
Figure 16:
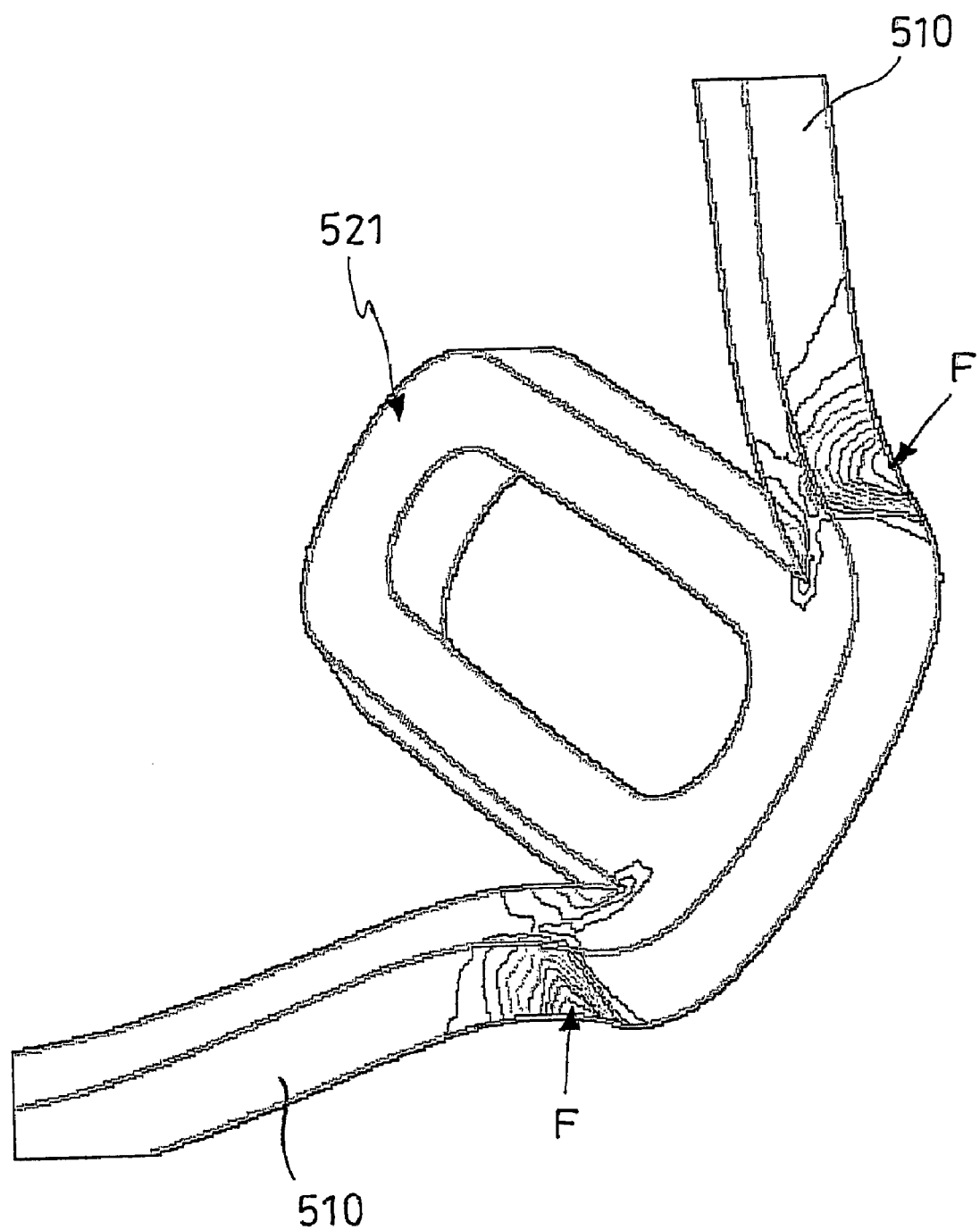
Figure 17:
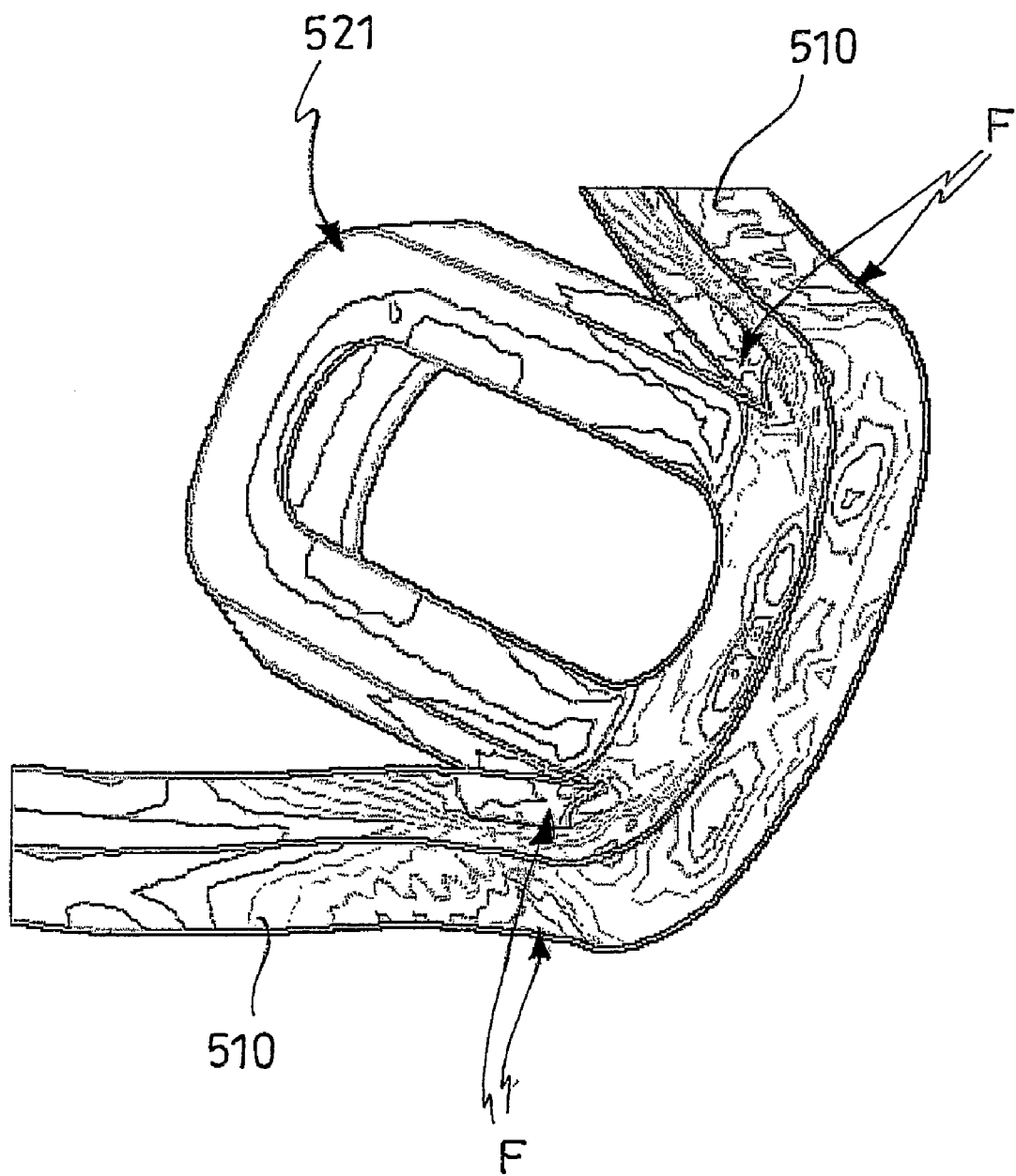
FIGS. 17 and 18 are perspective views of a detail of the prosthesis from FIG. 9 when expanded, wherein the stress condition and the corresponding strain condition are highlighted.
Figure 18:
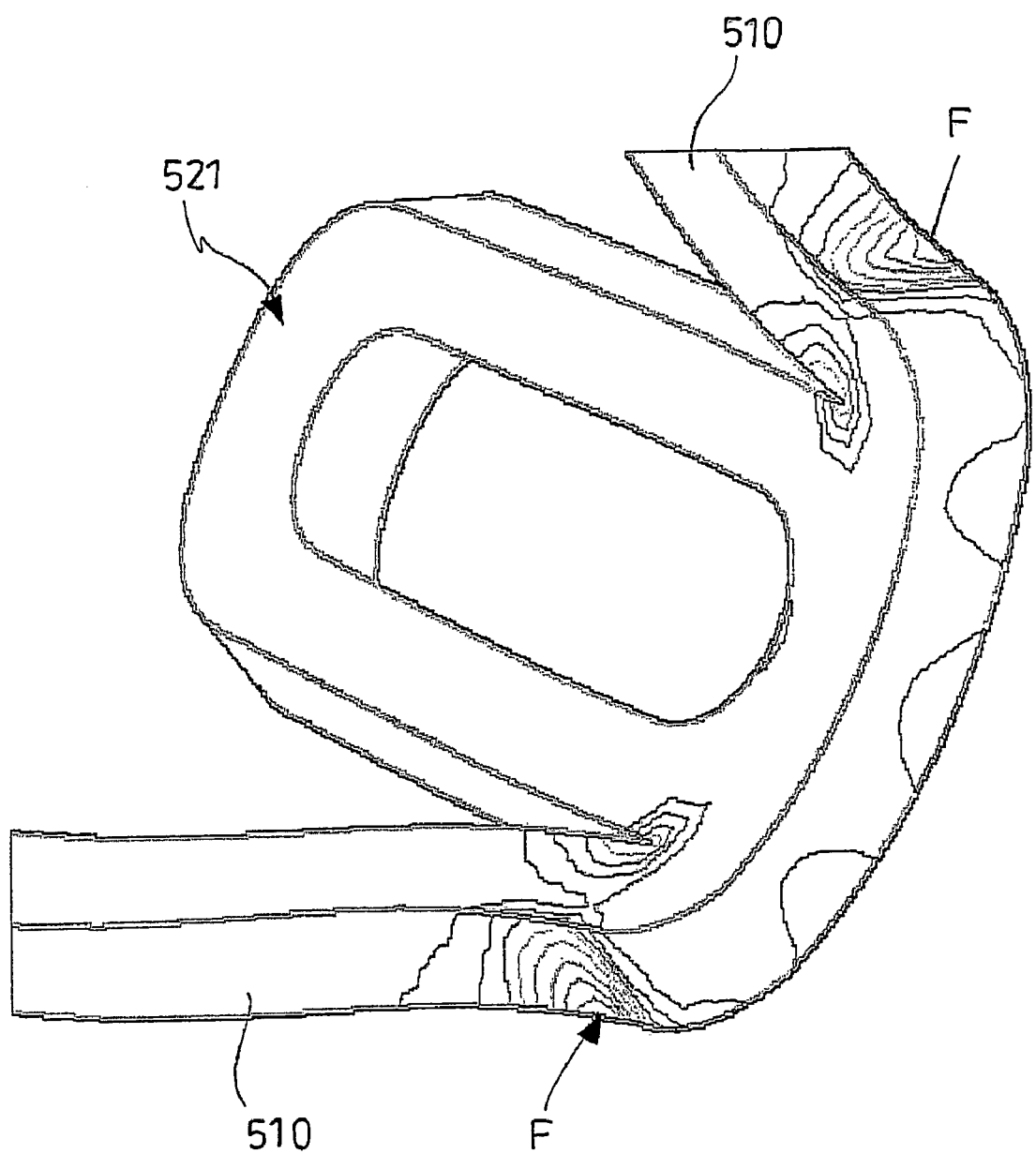
Figure 19:
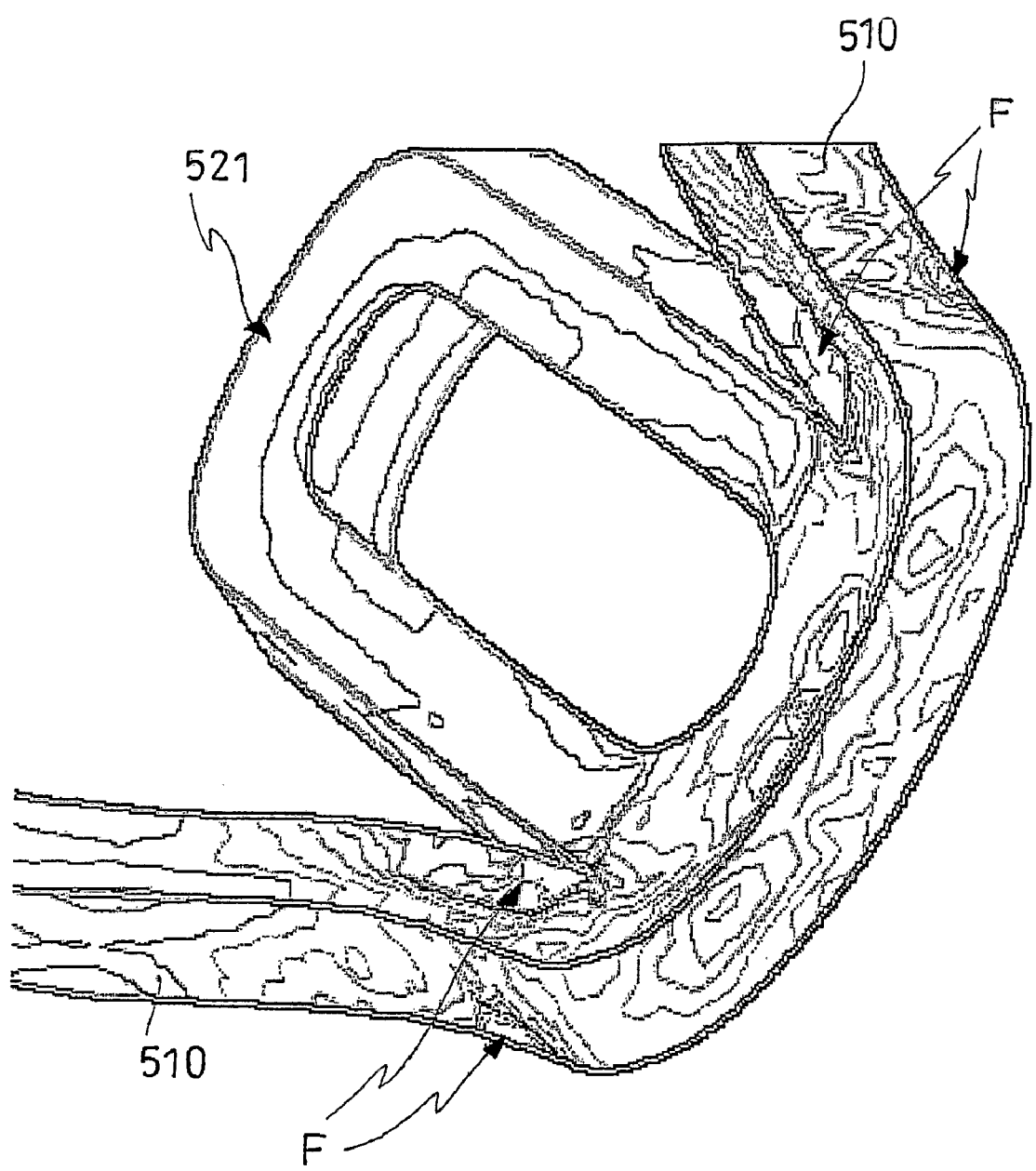
FIGS. 19 and 20 are a perspective view of a detail of the prosthesis from FIG. 11 when expanded, wherein the stress condition and the corresponding strain condition are highlighted.
Figure 20:
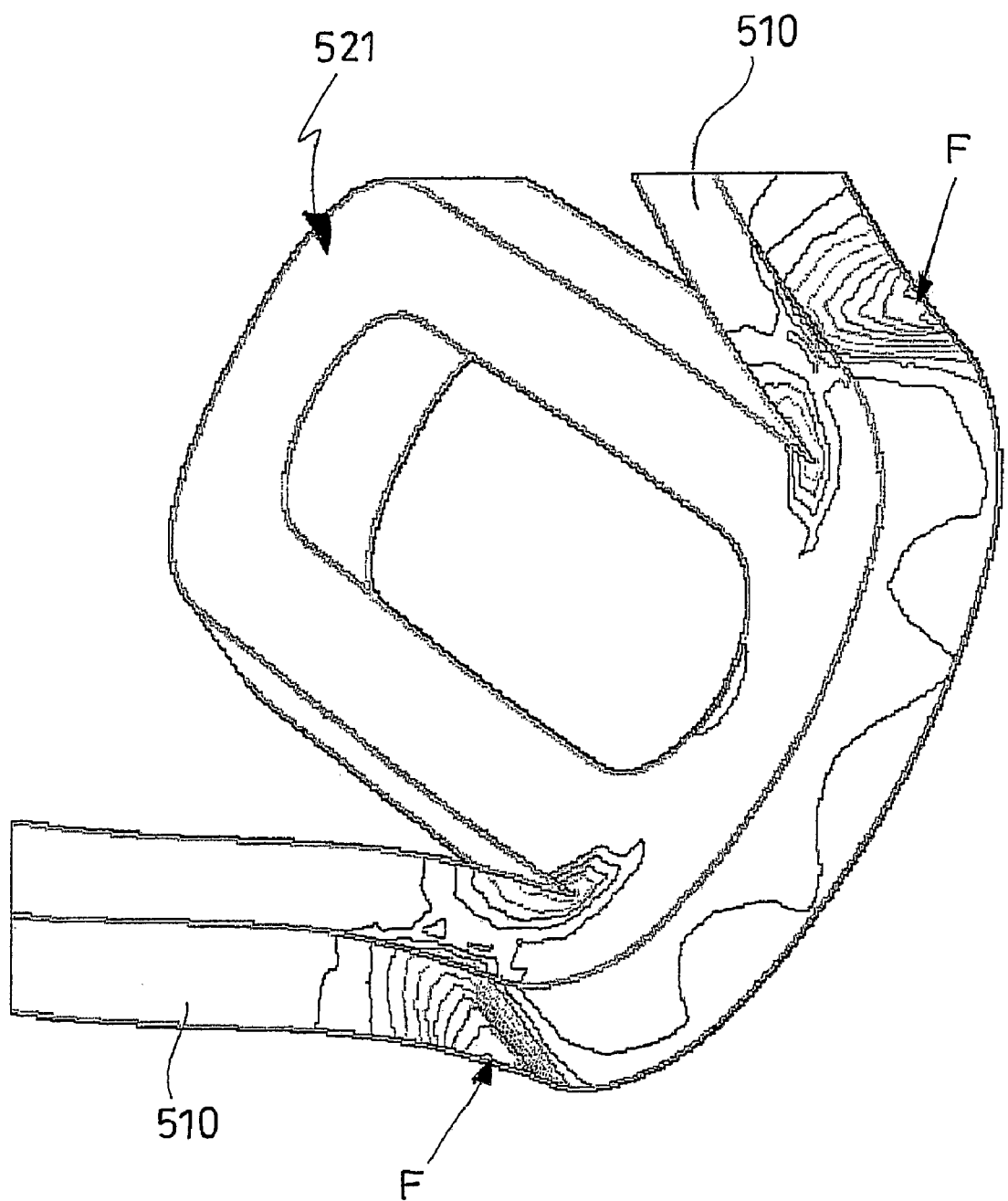

FIGS. 13, 14 illustrate the stresses and strains at the frame 521 in the prosthesis from FIGS. 3, 5, respectively. FIGS. 15, 16 illustrate the stresses and strains at the frame 521 in the prosthesis from FIGS. 7, 8, respectively. FIGS. 17, 18 illustrate the stresses and strains at the frame 521 in the prosthesis from FIGS. 9, 10, respectively. FIGS. 19, 20 illustrate the stresses and strains at the frame 521 in the prosthesis from FIG. 11, 12, respectively. Arrow F designates the greatest stress-strain area. The prosthesis illustrated in FIGS. 3, 5 allows to achieve a very low stress-strain peak value, and however a more constant distribution or gradual variation of the stress state.

The above has been achieved both by the advantageous embodiment of the frame 521 to accommodate the radiopaque material and by the overall synergy between the frame 521 and the overall geometry of the prosthesis.

Thanks to the prosthesis thus provided, it is possible to carry out endoluminal operations in tortuous vessels or ducts, and at the same time, an optimum and constant support of the treated vessel wall can also be ensured with the prosthesis being in the expanded state.

FIGS. 21 to 26 illustrate six release steps from a sheath 612 of a self-expanding endoluminal prosthesis 500. This procedure is, for example, carried out by withdrawing the sheath such that the prosthesis is left free to expand, such as from a housing where it is accommodated as provided in a transport and release device, such as a catheter (not shown herein).

It should be understood that variants and/or additions may be provided to what has been described and illustrated above.

The slot can be of any shape other than that illustrated in the figures. Furthermore, it could be provided in a serpentine different from the serpentine end, or in a bend corresponding to a valley with reference to the meaning of the term "valley" such as discussed above.

The number of serpentines, arms or bends may be changed from what has been described or illustrated. The shape of the serpentines may also be changed, particularly the alternate repetition between the second and third serpentines. For example, the second and third serpentines may be either equal, or perfectly symmetrical without resulting staggered in the circumferential direction.

Generally all the embodiments which have been described as possible above, can be made as such, in the absence of those characteristics described as belonging to other possible embodiments.

To the above preferred embodiments of the endoluminal prosthesis, those skilled in the art, aiming at satisfying contingent and specific needs, may carry out a number of modifications, variants and replacements of elements with others functionally equivalent, without departing from the scope of the claims below.

What is claimed is:

1. Endoluminal prosthesis, comprising
a tubular body suitable to turn from a collapsed state to an expanded or partially expanded state,
said body extending along a longitudinal axis,
said tubular body comprising a plurality of serpentines, or closed meander paths, extending along a substantially circumferential direction relative to said longitudinal axis,
each of said serpentines comprising arm portions, or arms, of a preset width transverse to the main longitudinal extension thereof,
each of said serpentines comprising bend portions, or bends, joining two subsequent arms to form said meander path,
at least one bridge having a main longitudinal extension, connecting two adjacent serpentines, thus forming at least two cells between said two adjacent serpentines, wherein
the bends facing an adjacent serpentine are circumferentially staggered relative to the opposite bends of the contiguous serpentine, both when the prosthesis is collapsed and when the prosthesis is expanded or partially expanded, wherein the at least one bridge connecting adjacent serpentines extends substantially straight, and wherein
the at least one bridge has a width transverse to its main longitudinal extension of a greater value than the arm width,
wherein at least one serpentine comprises at least one frame defining a slot located at the bend between two arms in place of at least two arms and one bend compared to a second serpentine,
a radiopaque material being provided within said slot.

2. Endoluminal prosthesis according to claim 1, wherein said at least one bridge joins with a bend of a serpentine and with a bend of an opposite serpentine.

3. Endoluminal prosthesis according to claim 1, wherein the at least one bridge has a substantially constant length all along the longitudinal extension thereof.

4. Endoluminal prosthesis according to claim 1, wherein the at least one bridge has a length substantially equal to twice the length of the arms.

5. Endoluminal prosthesis according to claim 1, wherein the at least one bridge has substantially straight edges.

6. Endoluminal prosthesis according to claim 1, wherein at least one bridge is comprised between all the adjacent serpentines.

7. Endoluminal prosthesis according to claim 1, wherein a plurality of bridges is comprised between adjacent serpentines.

8. Endoluminal prosthesis according to claim 1, wherein between at least two adjacent serpentines a bridge is provided every four bends as counted along the path of each serpentine.

9. Endoluminal prosthesis according to claim 1, wherein between at least two adjacent serpentines a bridge is provided every six bends as counted along the path of each serpentine.

10. Endoluminal prosthesis according to claim 1, wherein between at least two adjacent serpentines a bridge is provided every ten bends as counted along the path of each serpentine.

11. Endoluminal prosthesis according to claim 1, wherein the at least one bridge extends along a direction tangential to the tubular body and biased relative to an axis parallel to the longitudinal axis of said body.

12. Endoluminal prosthesis according to claim 1, wherein all the bridges between at least two adjacent serpentines are parallel to one another.

13. Endoluminal prosthesis according to claim 1, wherein by going through the prosthesis in a longitudinal way one encounters bridges which alternate with opposite way direction biases compared to an axis parallel to the longitudinal axis of the tubular body.

14. Endoluminal prosthesis according to claim 1, wherein by going through the prosthesis in a longitudinal way one encounters bridges alternating with direction biases of opposite value to that of an axis parallel to the longitudinal axis of the tubular body.

15. Endoluminal prosthesis according to claim 1, wherein a cell is comprised which comprises opposite lengths of two contiguous serpentines comprised between two subsequent bridges and said subsequent bridges to form a closed path.

16. Endoluminal prosthesis according to claim 1, wherein said arms are substantially straight.

17. Endoluminal prosthesis according to claim 1, wherein said arms comprise substantially straight edges.

18. Endoluminal prosthesis according to claim 15, wherein at least one cell comprises six complete bends.

19. Endoluminal prosthesis according to claim 15, wherein at least one cell comprises ten complete bends.

20. Endoluminal prosthesis according to claim 15, wherein at least one cell comprises eighteen complete bends.

21. Endoluminal prosthesis according to claim 1, wherein at least one prosthesis length in the collapsed state comprises a plurality of serpentines equal to one another with corresponding bends, facing the same prosthesis end, aligned with one another.

22. Endoluminal prosthesis according to claim 21, wherein said at least one prosthesis length is an intermediate portion of the prosthesis.

23. Endoluminal prosthesis according to claim 21, wherein said at least one prosthesis length is a middle length of the prosthesis.

24. Endoluminal prosthesis according to claim 1, wherein said prosthesis is a unique body.

25. Endoluminal prosthesis according to claim 1, wherein said body is obtained by cutting a tubular element.

26. Endoluminal prosthesis according to claim 1, wherein said body is obtained by laser cutting.

27. Endoluminal prosthesis according to claim 1, wherein said body is made of a superelastic material.

28. Endoluminal prosthesis according to claim 1, wherein said body is of a strain hardened pseudoelastic material.

29. Endoluminal prosthesis according to claim 1, wherein said body is of a shape memory material.

30. Endoluminal prosthesis according to claim 1, wherein said body is Nitinol.

31. Prosthesis according to claim 1, wherein said plurality of serpentines comprises a first serpentine and a second serpentine, said first serpentine forming only end lengths of said prosthesis.

32. Prosthesis according to claim 1, wherein said plurality of serpentines comprises a first serpentine, a second serpentine and a third serpentine, said second and third serpentines repeating alternatively along said longitudinal axis.

33. Endoluminal prosthesis according to claim 1, wherein said at least one serpentine is a first serpentine.

34. Endoluminal prosthesis according to claim 1, wherein said frame is located at the bend between two arms in place of four arms and three bends relative to the second or third serpentines.

35. Endoluminal prosthesis according to claim 1, wherein said frame is located in the concave part of the bend.

36. Endoluminal prosthesis according to claim 31, wherein said first serpentine is a prosthesis end serpentine.

37. Endoluminal prosthesis according to claim 1, wherein said frame is arranged at an end bend or peak of the serpentine.

38. Endoluminal prosthesis according to claim 1, wherein said frame is arranged within the corresponding cell as defined between the first serpentine and the second serpentine.

39. Endoluminal prosthesis according to claim 1, wherein said frame has an elongated shape in the direction of the prosthesis longitudinal axis.

40. Endoluminal prosthesis according to claim 1, wherein said frame extends from the end bend towards a middle axis of the endoluminal prosthesis.

41. Endoluminal prosthesis according to claim 1, wherein a cell comprising said frame is defined between the first and second serpentines, said cell comprising two bridges extending along two directions tangential to the tubular body which are incident to one another.

42. Endoluminal prosthesis according to claim 31, wherein between the first and second serpentines is defined a cell comprising said frame, said cell comprising two bridges extending along directions tangential to the tubular body, which are parallel to one another.

43. Endoluminal prosthesis according to claim 1, wherein the bridges of the cell comprising said frame extend along directions tangential to the tubular body converging from the end to a middle axis of the prosthesis.

44. Endoluminal prosthesis according to claim 1, wherein the bridges of the cell comprising said frame extend according to directions tangential to the tubular body which are biased relative to the longitudinal axis of the endoluminal prosthesis.

45. Endoluminal prosthesis according to claim 31, wherein the bridges connecting the first and second serpentines which do not belong to the cell comprising said frame are substantially parallel to one of both bridges belonging to the cell comprising said slot.

46. Endoluminal prosthesis according to claim 31, wherein in the cell comprising said frame the number of arms and bends of the first serpentine is smaller than the number of arms and bends of the second serpentine.

47. Endoluminal prosthesis according to claim 31, wherein in the cell comprising said frame the length belonging to the first serpentine comprises two arms and two bends less than the arms and bends belonging to the length belonging to the second serpentine, as symmetrically counted between both serpentines starting from the joining bridges.

48. Endoluminal prosthesis according to claim 31, wherein in the cell comprising said frame the length belonging to the first serpentine comprises six arms and five bends, whereas the length belonging to the second serpentine comprises eight arms and seven bends.

49. Endoluminal prosthesis according to claim 1, wherein said slot passes all through the thickness of the tubular body.

50. Endoluminal prosthesis according to claim 1, wherein said radiopaque material is either melted or welded within the slot.

51. Endoluminal prosthesis according to claim 32, wherein said second and third serpentines are symmetrical relative to a circumferential direction intermediate between both serpentines and staggered relative to one another.

52. Endoluminal prosthesis according to claim 1, wherein two frames are provided which are arranged in end serpentines of the prosthesis, respectively.

53. Endoluminal prosthesis according to claim 1, wherein the end serpentines are symmetrical to one another relative to a middle axis of the prosthesis.

54. Endoluminal prosthesis according to claim 1, wherein the end serpentines are symmetrical to one another relative to a middle axis of the prosthesis and staggered in the circumferential direction.

55. Endoluminal prosthesis according to claim 31, wherein at least an anomalous cell is provided being defined between the first and second serpentines, said anomalous cell being different from both the cell containing said frame and the remaining cells of the prosthesis.

56. Endoluminal prosthesis according to claim 55, wherein said anomalous cell is adjacent to the cell containing said frame, and shares a connecting bridge with it.

57. Endoluminal prosthesis according to claim 55, wherein the anomalous cell shares with the cell containing the frame the bridge extending along a direction tangential to the tubular body which is incident to the directions of development of the remaining bridges provided between the first and second serpentines.

58. Endoluminal prosthesis according to claim 55, wherein the anomalous cell comprises two arms and two bends more than the remaining cells of the prosthesis which do not contain the frame.

59. Endoluminal prosthesis according to claim 55, wherein the anomalous cell comprises six arms and five bends on the length corresponding to the second serpentine whereas the remaining cells of the prosthesis comprise, with reference to a length corresponding to a serpentine, four arms and three bends.

60. Endoluminal prosthesis according to claim 1, wherein said frame occupies the entire width which has been left free by the replaced arms and bends, as measured along the circumferential direction.

61. Endoluminal prosthesis according to claim 1, wherein said frame is formed as a unique body in the tubular body by laser cutting a cylindrical wall.

62. Endoluminal prosthesis according to claim 1, wherein said slot has an elongated shape along the direction of the prosthesis longitudinal axis.

63. Endoluminal prosthesis according to claim 1, wherein an end side of the frame is substantially straight along the circumferential direction, in a plane development of the prosthesis.

64. Endoluminal prosthesis according to claim 1, wherein those arms directly connected to the frame join thereto at end points of the frame itself.

65. Endoluminal prosthesis according to claim 1, wherein said frame comprises elongated sides of substantially the same width as the prosthesis arms, as measured along the circumferential direction, and a shorter length of the prosthesis arms, as measured along the longitudinal direction.

66. Endoluminal prosthesis according to claim 1, wherein a serpentine is closed along the circumferential direction relative to the prosthesis.

67. Endoluminal prosthesis comprising:
- a tubular body extending along a longitudinal axis, said tubular body comprising a plurality of serpentines or meander paths extending along a substantially circumferential direction relative to the direction of the longitudinal axis of the endoluminal prosthesis, said serpentines comprising arms connected by bends,
- wherein two adjacent serpentines are connected by at least one bridge thus forming at least two cells between said two adjacent serpentines,
- wherein at least one serpentine comprises at least one frame occupying a slot between two arms, said frame being opposite and in place of at least two arms and one bend on an adjacent serpentine,
- a radiopaque material being provided within said slot.

68. Prosthesis according to claim 67, wherein said plurality of serpentines comprises a first serpentine and a second serpentine, said first serpentine forming only end lengths of said prosthesis.

69. Prosthesis according to claim 67, wherein said plurality of serpentines comprises a first serpentine, a second serpentine and a third serpentine, said second and third serpentines alternatively repeating along said longitudinal axis.

70. Endoluminal prosthesis according to claim 67, wherein said at least one serpentine is a first serpentine.

71. Endoluminal prosthesis according to claim 69, wherein said frame is arranged at the bend between both arms in place of four arms and three bends relative to second or third serpentines.

72. Endoluminal prosthesis according to claim 67, wherein said frame is arranged on the concave part of the bend.

73. Endoluminal prosthesis according to claim 68, wherein said first serpentine is an end serpentine of the prosthesis.

74. Endoluminal prosthesis according to claim 73, wherein said frame is arranged at an end bend or peak of the serpentine.

75. Endoluminal prosthesis according to claim 74, wherein said frame is arranged within the corresponding cell as defined between the first and the second serpentines.

76. Endoluminal prosthesis according to claim 67, wherein said frame has an elongated shape in the direction of the longitudinal axis of the prosthesis.

77. Endoluminal prosthesis according to claim 76 when dependent from claim 5, wherein said frame extends from the end bend towards a middle axis of the endoluminal prosthesis.

78. Endoluminal prosthesis according to claim 67, wherein between the first and second serpentines a cell is defined which comprises said frame, said cell comprising two bridges extending along directions tangential to the tubular body, which are incident to one another.

79. Endoluminal prosthesis according to claim 67, wherein between the first and the second serpentine a cell is defined which comprises said frame, said cell comprising two bridges extending along directions tangential to the tubular body, which are parallel to one another.

80. Endoluminal prosthesis according to claim 78, wherein the bridges of the cell comprising said frame extend along directions tangential to the tubular body converging from the end to a middle axis of the prosthesis.

81. Endoluminal prosthesis according to claim 78, wherein the bridges of the cell comprising said frame extend according to directions tangential to the tubular body which are biased relative to the longitudinal axis of the endoluminal prosthesis.

82. Endoluminal prosthesis according to claim 78, wherein the connecting bridges between the first and second serpentines that do not belong to the cell comprising said frame are substantially parallel to one of those bridges belonging to the cell comprising said slot.

83. Endoluminal prosthesis according to claim 78, wherein in the cell comprising said frame the number of arms and bends of the first serpentine is lower than the number of arms and bends of the second serpentine.

84. Endoluminal prosthesis according to claim 83, wherein in the cell comprising said frame the length belonging to the first serpentine comprises two arms and two bends less than the arms and bends of the length belonging to the second serpentine, as symmetrically counted between both serpentines starting from junction points.

85. Endoluminal prosthesis according to claim 84, wherein in the cell comprising said frame the length belonging to the first serpentine comprises six arms and five bends whereas the length belonging to the second serpentine comprises eight arms and seven bends.

86. Endoluminal prosthesis according to claim 67, wherein said slot passes all through the thickness of the tubular body.

87. Endoluminal prosthesis according to claim 67, wherein said radiopaque material is either melted or welded within the slot.

88. Endoluminal prosthesis according to claim 69, wherein said second and third serpentines are symmetrical relative to a circumferential direction intermediate between both serpentines and staggered to one another.

89. Endoluminal prosthesis according to claim 67, wherein two frames are provided arranged in end serpentines of the prosthesis, respectively.

90. Endoluminal prosthesis according to claim 89, wherein the end serpentines are symmetrical to one another relative to a middle axis of the prosthesis.

91. Endoluminal prosthesis according to claim 90, wherein the end serpentines are symmetrical to one another relative to a middle axis of the prosthesis and staggered in the circumferential direction.

92. Endoluminal prosthesis according to claim 67, wherein at least one anomalous cell is provided being defined between the first and second serpentines, said anomalous cell being different both from the cell containing said frame and the remaining cells of the prosthesis.

93. Endoluminal prosthesis according to claim 92, wherein said anomalous cell is adjacent to the cell containing said frame, sharing a connecting bridge therewith.

94. Endoluminal prosthesis according to claim 93, wherein the anomalous cell shares with the cell containing the frame the bridge extending along a direction tangential to the tubular body incident to the directions of development of the remaining bridges provided between the first and second serpentines.

95. Endoluminal prosthesis according to claim 92, wherein the anomalous cell comprises two arms and two bends more than the remaining cells of the prosthesis which do not contain the frame.

96. Endoluminal prosthesis according to claim 95, wherein the anomalous cell comprises on the length corresponding to the second serpentine six arms and five bends, whereas the remaining cells of the prosthesis comprise, with reference to a length corresponding to a serpentine, four arms and three bends.

97. Endoluminal prosthesis according to claim 67, wherein said frame occupies the whole width which has been left free by the replaced arms and bends, as measured along the circumferential direction.

98. Endoluminal prosthesis according to claim 67, wherein said frame is formed as a unique body in the tubular body by laser cutting a cylindrical wall.

99. Endoluminal prosthesis according to claim 67, wherein said slot has an elongated shape along the direction of the longitudinal axis of the prosthesis.

100. Endoluminal prosthesis according to claim 67, wherein an end side of the frame is substantially straight along the circumferential direction, in a plane development of the prosthesis.

101. Endoluminal prosthesis according to claim 67, wherein the arms directly connected to the frame join thereto at end points of the frame itself.

102. Endoluminal prosthesis according to claim 67, wherein said frame comprises elongated sides having substantially the same width as the prosthesis arms, as measured along the circumferential direction, and the length being shorter than the prosthesis arms, as measured along the longitudinal direction.

103. Endoluminal prosthesis according to claim 67, wherein a serpentine is closed along the circumferential direction of the prosthesis.

* * * * *